(12) United States Patent
Finnie et al.

(10) Patent No.: US 10,183,020 B2
(45) Date of Patent: Jan. 22, 2019

(54) PHARMACEUTICAL COMPOSITIONS COMPRISING AZD9291

(71) Applicant: AstraZeneca AB, Sodertalje (SE)

(72) Inventors: Cindy Finnie, Macclesfield (GB); Steven Anthony Raw, Macclesfield (GB); David Wilson, Macclesfield (GB)

(73) Assignee: AstraZeneca AB, Södertälje (SE)

( * ) Notice: Subject to any disclaimer, the term of this patent is extended or adjusted under 35 U.S.C. 154(b) by 0 days.

(21) Appl. No.: 15/109,170

(22) PCT Filed: Jan. 2, 2015

(86) PCT No.: PCT/GB2015/050001
§ 371 (c)(1),
(2) Date: Jun. 30, 2016

(87) PCT Pub. No.: WO2015/101791
PCT Pub. Date: Jul. 9, 2015

(65) Prior Publication Data
US 2016/0324854 A1 Nov. 10, 2016

(30) Foreign Application Priority Data

Jan. 2, 2014 (GB) .................................. 1400034.3

(51) Int. Cl.
| | | |
|---|---|---|
| A61K 31/506 | (2006.01) | |
| A61K 9/28 | (2006.01) | |
| A61K 9/00 | (2006.01) | |
| A61K 9/20 | (2006.01) | |

(52) U.S. Cl.
CPC .......... *A61K 31/506* (2013.01); *A61K 9/0053* (2013.01); *A61K 9/2054* (2013.01); *A61K 9/28* (2013.01)

(58) Field of Classification Search
None
See application file for complete search history.

(56) References Cited

U.S. PATENT DOCUMENTS

| | | | |
|---|---|---|---|
| 2009/0017024 A1* | 1/2009 | Estok | A61K 31/05 514/1.1 |
| 2009/0028868 A1* | 1/2009 | Fujiwara | A61K 31/427 424/141.1 |

FOREIGN PATENT DOCUMENTS

| | | |
|---|---|---|
| WO | 03072139 A1 | 9/2003 |
| WO | 02083653 A1 | 10/2004 |
| WO | 2012139736 A1 | 10/2012 |

(Continued)

OTHER PUBLICATIONS

International Search Report issued for PCT/GB2015/050001 dated Mar. 6, 2015.

(Continued)

*Primary Examiner* — Aradhana Sasan
(74) *Attorney, Agent, or Firm* — Meaghan Lynn Richmond

(57) ABSTRACT

The present invention relates to pharmaceutical compositions suitable for oral administration, and more particularly to pharmaceutical compositions, including pharmaceutical tablet compositions, containing N-(2-{2-dimethylaminoethyl-methyl-amino}-4-methoxy-5-{[4-(1-methylindol-3-yl)pyrimidin-2-yl]amino}phenyl)prop-2-enamide ("AZD9291") or a pharmaceutically acceptable salt thereof, wherein such compositions comprise a certain amount of microcrystalline cellulose and at least one other pharmaceutical diluent.

23 Claims, 6 Drawing Sheets

(56) References Cited

FOREIGN PATENT DOCUMENTS

| | | |
|---|---|---|
| WO | 2012169733 A1 | 12/2012 |
| WO | 2013014448 A1 | 1/2013 |
| WO | 2013160916 A1 | 10/2013 |

OTHER PUBLICATIONS

Written Opinion issued for PCT/GB2015/050001 dated Mar. 6, 2015.
Garcia, J.L.L. "Nuevos sistemas orales de liberacion modificada", Schironia, 2002, p. 63-71, English Summary only.

* cited by examiner

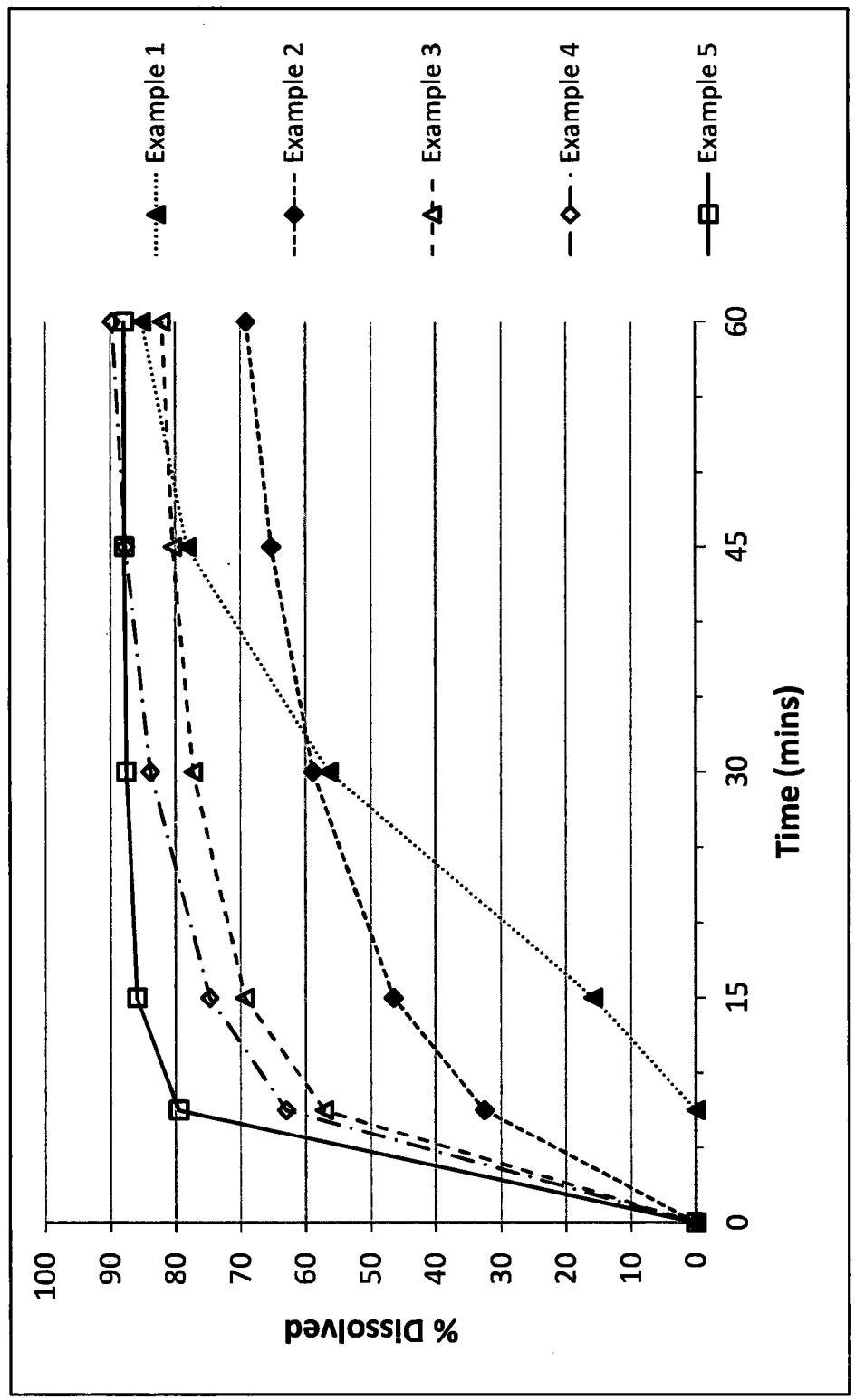
Figure 1 - Dissolution profile for Examples 1 to 5 (pH 6.8)

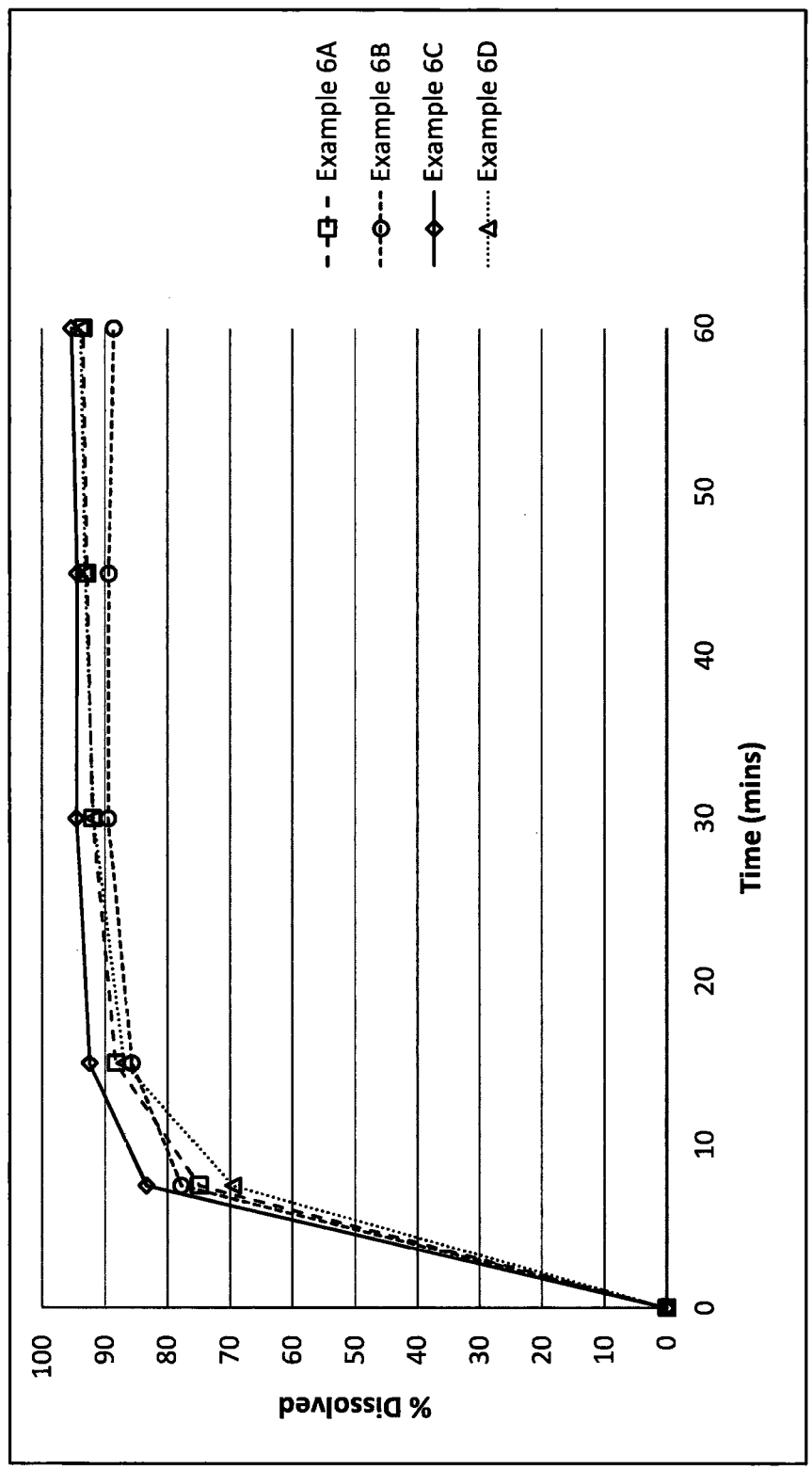
Figure 2 - Dissolution profile for Examples 6A, 6B, 6C and 6D (pH 6.8)

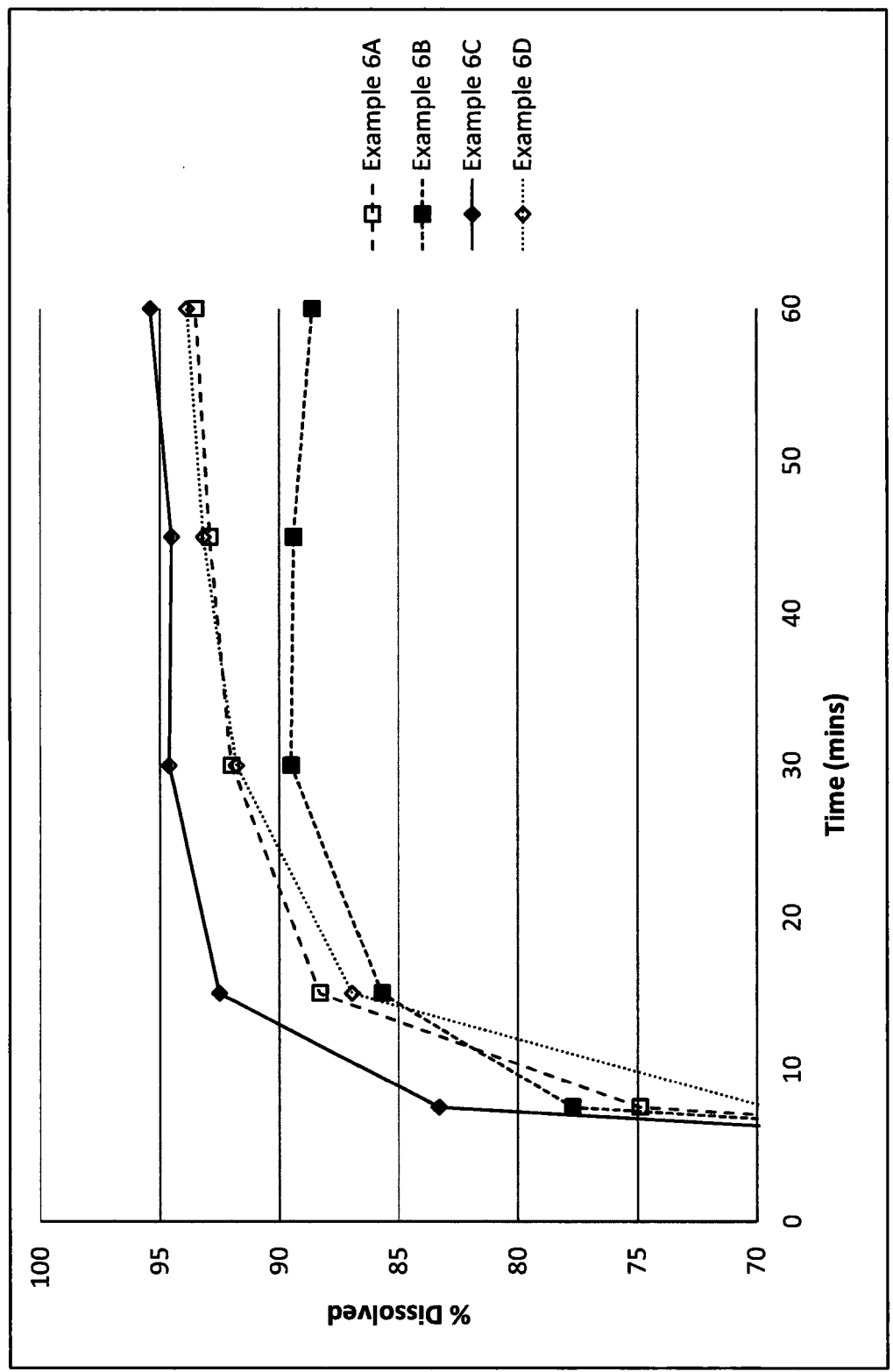
Figure 3 - Expanded dissolution profile for Examples 6A, 6B, 6C and 6D (pH 6.8)

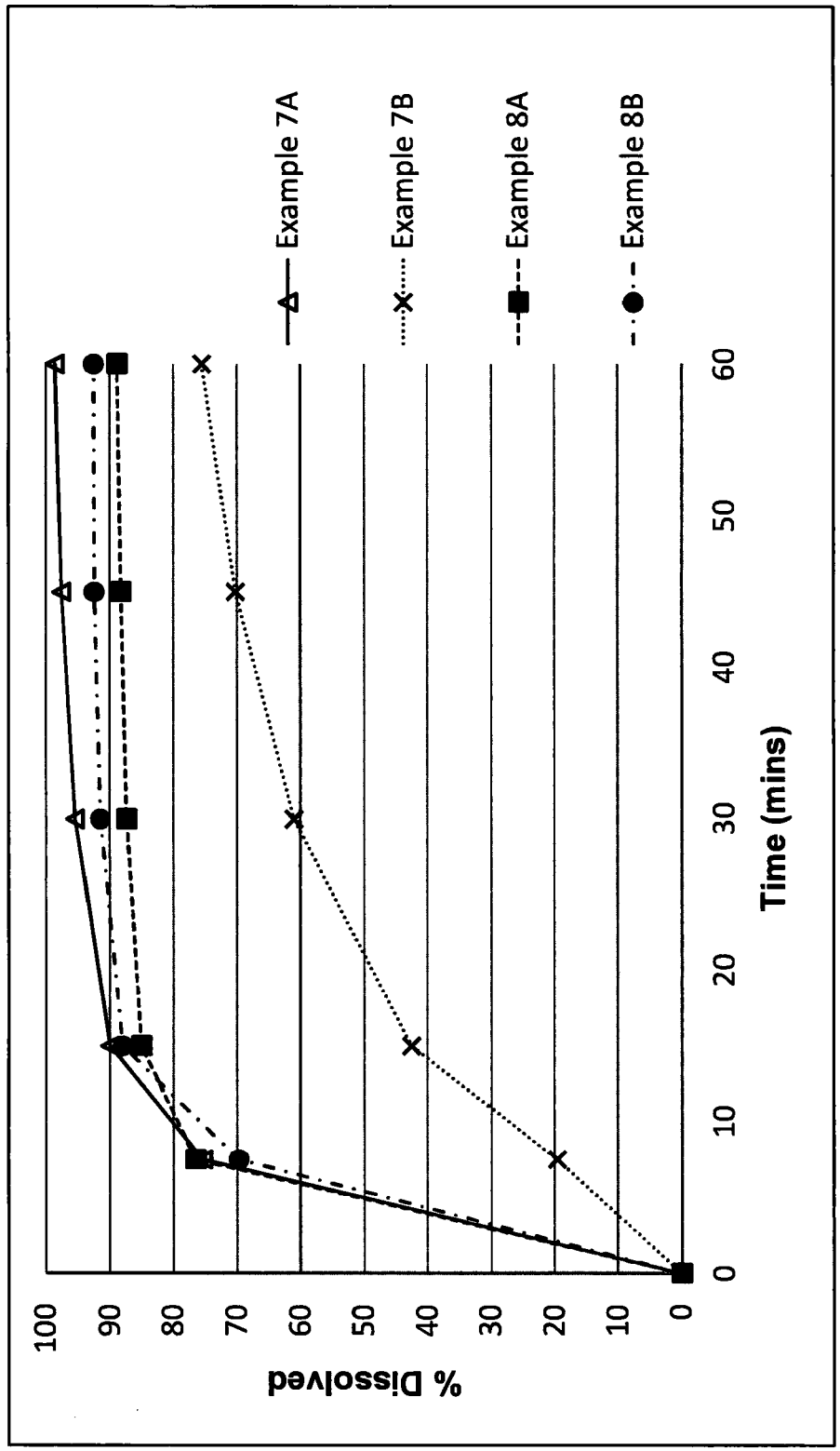
Figure 4 - Dissolution profile for Examples 7A, 7B, 8A and 8B (pH 6.8)

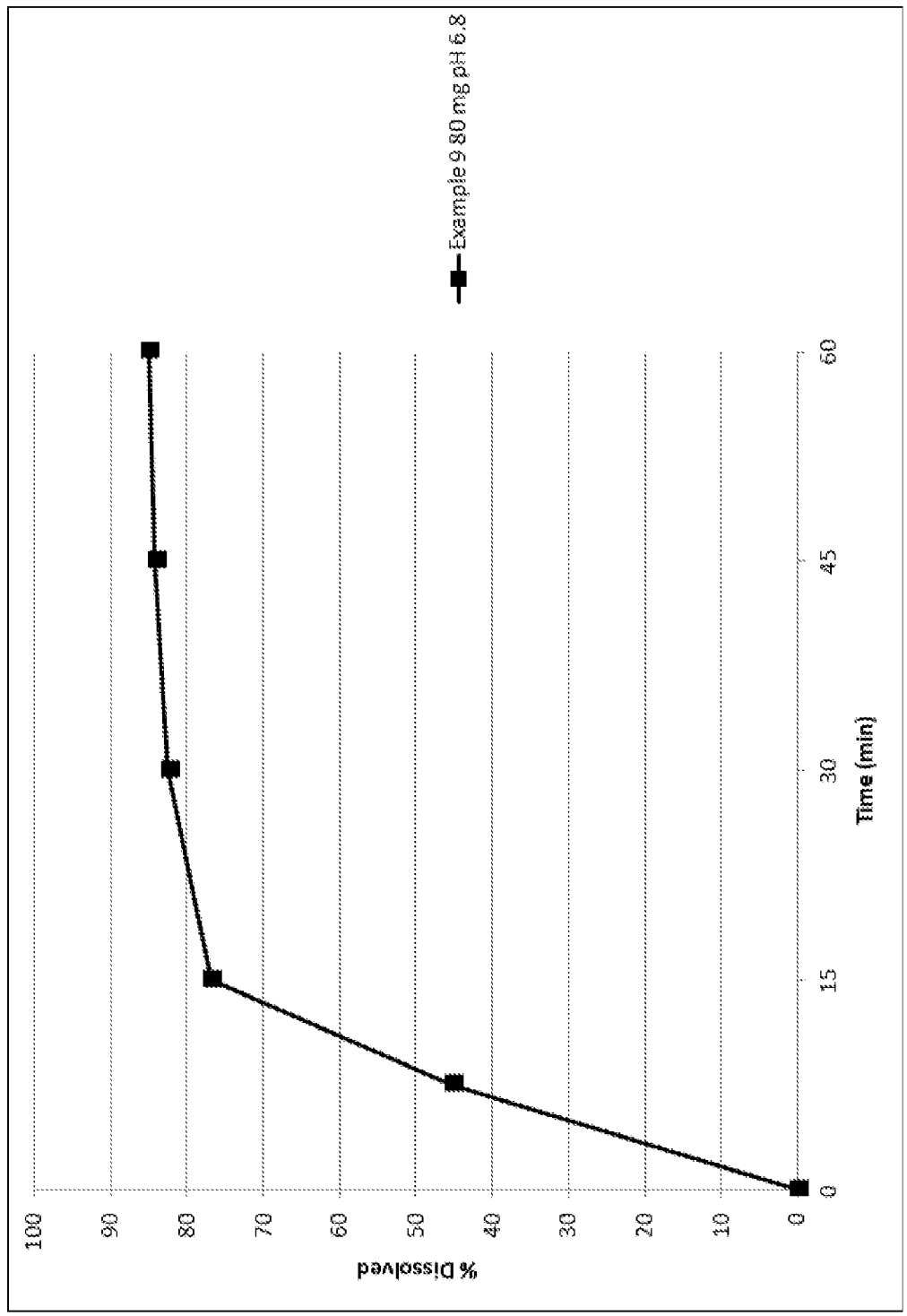
Figure 5 - Dissolution profile for Example 9 (80mg, pH 6.8)

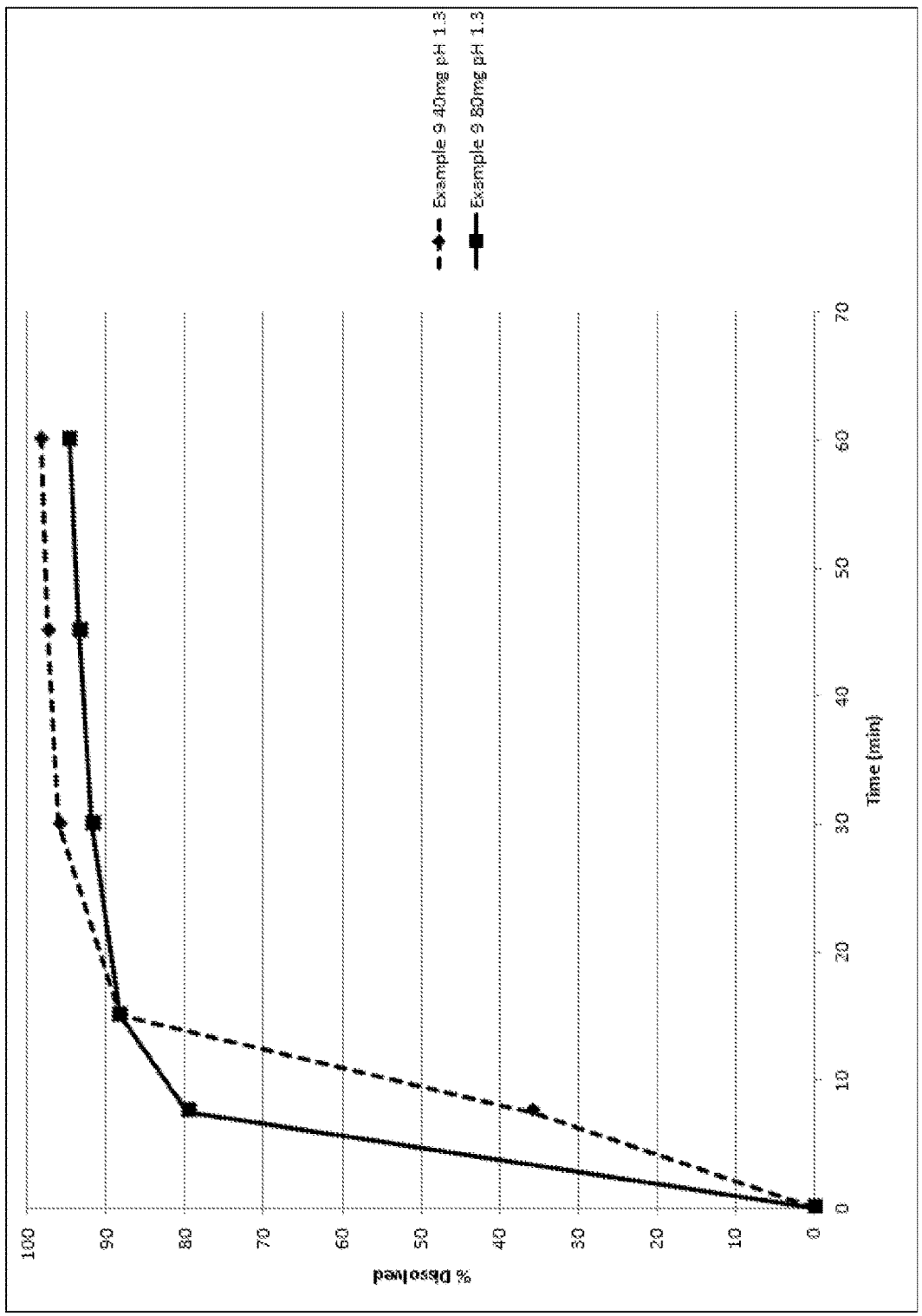
Figure 6 - Dissolution profile for Example 9 (pH 1.3)

PHARMACEUTICAL COMPOSITIONS COMPRISING AZD9291

The present invention relates to pharmaceutical compositions suitable for oral administration, and more particularly to pharmaceutical compositions (and pharmaceutical tablets) containing the compound known as "AZD9291":

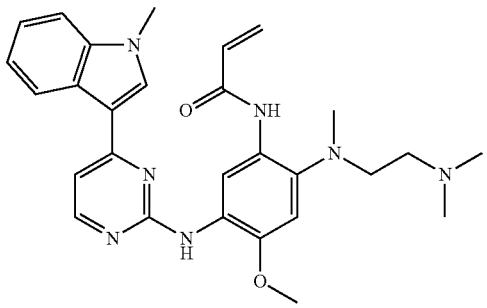 [SMILES: C=CC(=O)Nc1cc(Nc2nccc(-c3cn(C)c4ccccc34)n2)c(OC)cc1N(C)CCN(C)C]

or a pharmaceutically acceptable salt thereof.

AZD9291 is also known by the chemical name: 'N-(2-{2-dimethylaminoethyl-methylamino}-4-methoxy-5-{[4-(1-methylindol-3 -yl)pyrimidin-2-yl]amino}phenyl)prop-2-enamide' AZD9291 or a pharmaceutically acceptable salt thereof is hereinafter referred to as the "Agent".

The Agent is disclosed in international patent application number PCT/GB2012/051783 (publication number WO2013/014448) where data is provided to show that the Agent selectively and potently inhibits certain mutant forms of epidermal growth factor receptor (EGFR). It has been found that the Agent is a potent inhibitor of both the EGFRm+ sensitising and the T790M resistance mutant forms of EGFR while having much lower potency against wild-type EGFR. In vitro, the Agent potently inhibits EGFR signaling pathways and cellular growth in both EGFRm+ and T790M mutant cell lines with much less activity against wild-type EGFR lines. In vivo, inhibition of EGFR signaling by the Agent causes profound and sustained tumor regression of both EGFRm+ and T790M mutant tumour xenograft and transgenic models, at doses as low as 5 mg/kg/day. In a phase 1 clinical trial, a number of patients with advanced EGFRm T790M+ lung adenocarcinoma showed partial responses after treatment with the Agent (in this case, the Agent was used in the form of the mesylate salt). The pharmaceutical formulation used initially (in the Phase 1 clinical trial) involved a simple blend of AZD9291 mesylate salt with microcrystalline cellulose which was then filled into HPMC capsules. Further details of this 'blend in capsule' formulation are described hereinafter as 'Comparative Example 1'.

Typically, a drug may be absorbed in a number of different sites along the gastrointestinal tract following oral administration, including via the stomach, duodenum, jejunum, ileum and colon. The pH may be different at each site of absorption with the pH varying significantly between the stomach (pH 1-3.5) and the small intestine (pH 4-8). From our studies we have found that AZD9291 exhibits significant pH dependent solubility and moderate permeability. For example, AZD9291 (in free base form) has been found to have >80× higher solubility in simulated gastric fluid (SGF, pH=1.3) relative to human intestinal fluid (HIF, pH=7.9). In such cases, where the solubility of a drug varies with pH, and particularly when the solubility is highest at acidic pH, there is a problem that the drug may precipitate from solution as it passes through the gastrointestinal tract. Drugs need to be in solution in order to be absorbed, so such precipitation can lead to variability in the extent and/or rate of absorption of the drug. This leads to the problem that the amount of a drug reaching a patient's systemic circulation can vary significantly between one dose and the next in a given patient. It can also lead to the problem that the amount of drug reaching a patient's systemic circulation can vary significantly between one patient and another. If a patient effectively receives a lower dose than was intended by their physician as a result of such variability of absorption, it may mean that the drug is less effective than it could be for improving the patient's condition. In principle, the dose administered to a patient could be increased to account for potentially poor absorption, but this approach introduces a risk that too much of the drug may enter the patient's system in some cases—which may be a safety risk and/or increase the risk/severity of side-effects. For the mesylate salt of AZD9291 we found that the solubility at intestinal pH is significantly higher than that of AZD9291 in free base form. A solution of AZD9291 mesylate, once formed, appeared to be stable without precipitation over a period of at least 24 hours. Based on these and other studies, a simple 'blend in capsule' formulation of AZD9291 mesylate with microcrystalline cellulose was expected to have favourable characteristics including rapid and complete dissolution across the physiological pH range, and accordingly, it was hoped that the use of the mesylate salt of AZD9291 in a simple 'blend in capsule' formulation with microcrystalline cellulose would avoid all of the above-mentioned problems. However, unfortunately we found that simple 'blend in capsule' formulation of AZD9291 mesylate with microcrystalline cellulose (Comparative Example 1) dissolved very slowly following the expected time lag associated with disruption of the capsule shell, achieving only 56.4% release after 30 minutes at pH 6.8. Accordingly, there remained a problem to provide an improved way of dosing the Agent to patients that should reduce/avoid the risk of and/or severity of the above-mentioned problems of inter-patient variability of absorption and/or inter-dose variability of absorption.

The present invention provides a solution to one or more of the above-mentioned problems and involves a novel pharmaceutical composition containing the Agent. The pharmaceutical composition of the present invention may be formed into tablets which exhibit improved dissolution characteristics under physiologically relevant conditions, and/or a higher overall release of the Agent on a physiologically relevant timescale. Achieving a faster initial dissolution rate and/or a higher overall release of the Agent is expected to reduce the risk of inter-dose and inter-patient variability of absorption for a drug that has the pH dependent solubility as exhibited by AZD9291.

Accordingly, in the first aspect of the invention there is provided a pharmaceutical composition that delivers a significantly improved level of dissolution of the Agent after 15 minutes in solution at pH 6.8. Dissolution measurements were carried out using the general procedure of the United State Pharmacopoeia using Apparatus II at pH 6.8 or 1.3 as described in further detail in the Experimental section hereinafter. Each entry in the table below is based on an average of three dissolution measurements at pH 6.8, where Comparative Example 1 is the 'blend in capsule' formulation, and where the other Examples are Examples of the first aspect of the present invention:

| Example No. | Percent dissolved at t = 15 mins |
|---|---|
| Comparative Ex. 1 | 15.8 |
| 2 | 46.5 |
| 3 | 69.4 |
| 4 | 74.7 |
| 5 | 86.0 |
| 6A | 88.3 |
| 6B | 85.7 |
| 6C | 92.5 |
| 6D | 86.9 |
| 7A | 89.9 |
| 7B | 42.5 |
| 8A | 85.0 |
| 8B | 88.0 |
| 9 | 76.9 |

Whilst Comparative Example 1 involved the use of microcrystalline cellulose as the one and only pharmaceutical diluent, we have found that the improved pharmaceutical compositions of the present invention (e.g. Examples 2-9) involve the use of a much lower wt % of microcrystalline cellulose and the use of at least one other pharmaceutically acceptable diluent substance in combination with the microcrystalline cellulose.

Accordingly, in the first aspect of the invention there is provided a pharmaceutical composition comprising:
(a) from 2 to 70 parts of the Agent;
(b) from 5 to 96 parts of two or more pharmaceutical diluents;
(c) from 0 to 15 parts of one or more pharmaceutical disintegrants;
(d) from 0 to 1.5 parts of one or more pharmaceutical solubilising agents; and
(e) from 0 to 3 parts of one or more pharmaceutical lubricants;
wherein all parts are by weight and the sum of the parts (a)+(b)+(c)+(d)+(e)=100; and wherein one of the two or more pharmaceutical diluents is microcrystalline cellulose wherein the microcrystalline cellulose makes up from 7 to 30 wt % of the two or more pharmaceutical diluents (b).

In this specification 'wt %' refers to 'weight percent' and is intended to have its ordinary meaning as is customary in the technical field. Accordingly, 'wt %' refers to a proportion of Component X within Composition Y, in each case calculated based on the weights of Component X and Composition Y (as opposed to other physical parameters, such as the volume or number of moles present). By way of example, if there is 2 g of Component X within 20 g of Composition Y then Component X makes up 10 wt % of Composition Y.

As described herein, the components of the pharmaceutical composition are described in terms of 'parts', where 'all parts are by weight'. It is to be understood that such language simply defines a relative ratio of the components, where the ratio is defined in terms of relative weights (as opposed to other physical parameters, such as the volume or number of moles present). By way of example, if there is 1 g of Component X and 4 g of Component Z in a mixture where the sum of the parts of Component X and Component Z are defined as being equal to 100, then in this example there are 20 parts of Component X and 80 parts of Component Z in the mixture.

In one embodiment the microcrystalline cellulose makes up from 12 to 28 wt % of the two or more pharmaceutical diluents (b).

In a further embodiment the microcrystalline cellulose makes up from 15 to 25 wt % of the two or more pharmaceutical diluents (b).

In a further embodiment the microcrystalline cellulose makes up from 17 to 23 wt % of the two or more pharmaceutical diluents (b).

The Agent

As defined hereinabove, the 'Agent' refers to 'AZD9291 or a pharmaceutically acceptable salt thereof'.

A pharmaceutically acceptable salt of AZD9291 may be formed using an inorganic or organic acid. A pharmaceutically acceptable salt may be formed, for example, using an inorganic acid, for example selected from hydrochloric acid, hydrobromic acid, sulphuric acid and phosphoric acid. A pharmaceutically acceptable salt may also be formed using an organic acid, for example selected from trifluoroacetic acid, citric acid, maleic acid, oxalic acid, acetic acid, formic acid, benzoic acid, fumaric acid, succinic acid, tartaric acid, lactic acid, pyruvic acid, methanesulfonic acid, benzenesulfonic acid and para-toluenesulfonic acid.

The Agent may be used in the 'free base form' or as a pharmaceutically acceptable salt, or as any mixture thereof. In one embodiment the Agent is in the free base form. It is understood that 'free base form' refers to the case where the Agent is not in the form of a salt.

In any claim, aspect or embodiment of the invention where the Agent is mentioned in a general sense the following embodiments may also be applied in order to provide further claims, aspects or embodiments:

In one embodiment the Agent is AZD9291 (i.e. AZD9291 in free base form).

In one embodiment the Agent is a pharmaceutically acceptable salt of AZD9291.

In one embodiment the Agent is a pharmaceutically acceptable salt of AZD9291 which is the mesylate salt of AZD9291.

In one embodiment the mesylate salt of AZD9291 contains a 1:1 molar ratio of AZD9291 with methanesulfonic acid.

In one embodiment the Agent is a pharmaceutically acceptable salt of AZD9291 which is a crystalline mesylate salt of AZD9291.

In one embodiment the Agent is polymorphic Form B of the mesylate salt of AZD9291 (wherein polymorphic Form B of the mesylate salt of AZD9291 may be defined in any of the ways described in international patent application number PCT/GB2012/051783/publication number WO2013/014448).

Therefore, in one embodiment the Agent is the mesylate salt of AZD9291 which has an X-ray powder diffraction pattern with at least one specific peak at 2-theta=7.2° plus or minus 0.2° 2-theta, measured using CuKα radiation.

In one embodiment the Agent is the mesylate salt of AZD9291 which has an X-ray powder diffraction pattern with at least one specific peak at 2-theta=8.6° plus or minus 0.2° 2-theta, measured using CuKα radiation.

In one embodiment the Agent is the mesylate salt of AZD9291 which has an x-ray powder diffraction pattern with at least two specific peaks at 2-theta=7.2° and 8.6°, wherein said values may be plus or minus 0.2° 2-theta, measured using CuKα radiation.

In one embodiment the Agent is the mesylate salt of AZD9291 which has an x-ray powder diffraction pattern with specific peaks at 2-theta=7.2, 8.6, 15.3, 10.4, 25.7, 26.1, 16.4, 9.5, 22.1 and 18.8° 2-theta, wherein said values may be plus or minus 0.2° 2-theta, measured using CuKα radiation.

In further embodiments of the invention the pharmaceutical composition (or pharmaceutical tablet) as defined herein may have the amount of the Agent (a) limited to any of the ranges listed below:
from 3 to 70 parts by weight
from 4 to 65 parts by weight
from 5 to 50 parts by weight
from 5 to 40 parts by weight
from 6 to 35 parts by weight
from 7 to 30 parts by weight
from 7 to 25 parts by weight
from 3 to 30 parts by weight Pharmaceutical Diluents In this specification the terms "diluent" and "diluents" are intended to be interpreted in the context of pharmaceutical formulation science. Accordingly, in addition to microcrystalline cellulose, other diluents may be, for example: calcium carbonate, calcium phosphate, calcium sulfate, cellulose acetate, erythritol, ethylcellulose, fructose, inulin, isomalt, lactitol, lactose, magnesium carbonate, magnesium oxide, maltitol, maltodextrin, maltose, mannitol, polydextrose, polyethylene glycol, pullulan, simethicone, sodium bicarbonate, sodium carbonate, sodium chloride, sorbitol, starch, sucrose, trehalose and xylitol.

Accordingly, in one embodiment of the invention in addition to microcrystalline cellulose, the other pharmaceutical diluent(s) within the two or more pharmaceutical diluents is/are selected from calcium carbonate, calcium phosphate, calcium sulfate, cellulose acetate, erythritol, ethylcellulose, fructose, inulin, isomalt, lactitol, lactose, magnesium carbonate, magnesium oxide, maltitol, maltodextrin, maltose, mannitol, polydextrose, polyethylene glycol, pullulan, simethicone, sodium bicarbonate, sodium carbonate, sodium chloride, sorbitol, starch, sucrose, trehalose and xylitol.

When the Agent is present in the pharmaceutical composition or (pharmaceutical tablet) in the form of a pharmaceutically acceptable salt of AZD9291, certain basic salts are less favoured for use as a pharmaceutical diluent. Such basic salts include calcium carbonate, magnesium carbonate, sodium carbonate and sodium bicarbonate. Accordingly in one embodiment of the invention (particularly when the Agent is a pharmaceutically acceptable salt of AZD9291) in addition to microcrystalline cellulose, the other pharmaceutical diluent(s) within the two or more pharmaceutical diluents is/are selected from calcium phosphate, calcium sulfate, cellulose acetate, erythritol, ethylcellulose, fructose, inulin, isomalt, lactitol, lactose, magnesium oxide, maltitol, maltodextrin, maltose, mannitol, polydextrose, polyethylene glycol, pullulan, simethicone, sodium chloride, sorbitol, starch, sucrose, trehalose and xylitol.

In one embodiment (particularly when the Agent is a pharmaceutically acceptable salt of AZD9291) in addition to microcrystalline cellulose, the other pharmaceutical diluent(s) within the two or more pharmaceutical diluents is/are selected from cellulose acetate, erythritol, ethylcellulose, fructose, inulin, isomalt, lactitol, lactose, maltitol, maltodextrin, maltose, mannitol, polydextrose, polyethylene glycol, pullulan, simethicone, sodium chloride, sorbitol, starch, sucrose, trehalose and xylitol.

In certain embodiments of the invention the pharmaceutical composition (or pharmaceutical tablet), as defined herein, may have the amount of the pharmaceutical diluent (b) limited to any of the ranges listed below:
from 10 to 95 parts by weight
from 15 to 90 parts by weight
from 20 to 90 parts by weight
from 25 to 90 parts by weight
from 30 to 90 parts by weight
from 40 to 90 parts by weight
from 50 to 90 parts by weight
from 60 to 90 parts by weight
from 40 to 80 parts by weight
from 50 to 80 parts by weight
from 55 to 85 parts by weight In one embodiment, in addition to the microcrystalline cellulose, the two or more pharmaceutical diluents (b) comprises one or more pharmaceutical diluents selected from mannitol, sorbitol, isomalt, polydextrose, lactitol and lactose.

In one embodiment, in addition to the microcrystalline cellulose, the two or more pharmaceutical diluents (b) comprises mannitol, sorbitol, isomalt, polydextrose, lactitol or lactose, or any mixture thereof, wherein the mannitol, sorbitol, isomalt, polydextrose, lactitol or lactose or any mixture thereof makes up from 50 to 100 wt % of the portion of two or more pharmaceutical diluents (b) that is not already accounted for by the presence of microcrystalline cellulose, as defined herein.

In one embodiment the aforementioned range is from 60 to 100 wt %.

In another embodiment the aforementioned range is from 70 to 100 wt %.

In another embodiment the aforementioned range is from 80 to 100 wt %.

In another embodiment the aforementioned range is from 90 to 100 wt %.

In another embodiment, in addition to the microcrystalline cellulose, the two or more pharmaceutical diluents (b) comprises mannitol, sorbitol, isomalt, polydextrose, lactitol or lactose, or any mixture thereof, wherein the mannitol, sorbitol, isomalt, polydextrose, lactitol or lactose or any mixture thereof makes up 100 wt % of the portion of two or more pharmaceutical diluents (b) that is not already accounted for by the presence of microcrystalline cellulose, as defined herein.

In one embodiment, in addition to the microcrystalline cellulose, the two or more pharmaceutical diluents (b) comprises mannitol, lactose or a mixture thereof.

In one embodiment, in addition to the microcrystalline cellulose, the two or more pharmaceutical diluents (b) comprises mannitol, lactose or a mixture thereof, wherein the mannitol or lactose or mixture thereof makes up from 50 to 100 wt % of the portion of two or more pharmaceutical diluents (b) that is not already accounted for by the presence of microcrystalline cellulose, as defined herein.

In one embodiment the aforementioned range is from 60 to 100 wt %.

In another embodiment the aforementioned range is from 70 to 100 wt %.

In another embodiment the aforementioned range is from 80 to 100 wt %.

In another embodiment the aforementioned range is from 90 to 100 wt %.

In another embodiment, in addition to the microcrystalline cellulose, the two or more pharmaceutical diluents (b) comprises mannitol or lactose or a mixture thereof, wherein the mannitol, lactose or mixture thereof makes up 100 wt % of the portion of two or more pharmaceutical diluents (b) that is not already accounted for by the presence of microcrystalline cellulose, as defined herein.

In one embodiment, in addition to the microcrystalline cellulose, the two or more pharmaceutical diluents (b) comprises mannitol.

In one embodiment, in addition to the microcrystalline cellulose, the two or more pharmaceutical diluents (b) comprises mannitol, wherein the mannitol makes up from 50 to 100 wt % of the portion of two or more pharmaceutical diluents (b) that is not already accounted for by the presence of microcrystalline cellulose, as defined herein.

In one embodiment the aforementioned range is from 60 to 100 wt %.

In another embodiment the aforementioned range is from 70 to 100 wt %.

In another embodiment the aforementioned range is from 80 to 100 wt %.

In another embodiment the aforementioned range is from 90 to 100 wt %.

In another embodiment, in addition to the microcrystalline cellulose, the two or more pharmaceutical diluents (b) comprises mannitol, wherein the mannitol makes up 100 wt % of the portion of two or more pharmaceutical diluents (b) that is not already accounted for by the presence of microcrystalline cellulose, as defined herein.

The embodiment described directly above mentions that 'mannitol makes up 100 wt % of the portion of the two or more pharmaceutical diluents (b) that is not already accounted for by the presence of microcrystalline cellulose'. Accordingly, for example, in the situation where the microcrystalline cellulose made up 30 wt % of the 'two or more pharmaceutical diluents (b)', the mannitol would have to make up 70 wt % of the 'two or more pharmaceutical diluents (b)' in order to meet the requirement that 'mannitol makes up 100 wt % of the portion of the two or more pharmaceutical diluents (b) that is not already accounted for by the presence of microcrystalline cellulose'.

Pharmaceutical Disintegrants

In this specification the terms "disintegrant" and "disintegrants" are intended to be interpreted in the context of pharmaceutical formulation science. Accordingly, a disintegrant may be, for example: alginic acid, calcium alginate, carboxymethylcellulose calcium, chitosan, colloidal silicon dioxide, croscarmellose sodium, crospovidone, glycine, guar gum, hydroxypropyl cellulose, low-substituted hydroxypropyl cellulose, magnesium aluminum silicate, methylcellulose, povidone, sodium alginate, sodium carboxymethylcellulose, sodium starch glycolate and starch.

Accordingly, in one embodiment the one or more pharmaceutical disintegrants comprises one or more pharmaceutical disintegrants selected from alginic acid, calcium alginate, carboxymethylcellulose calcium, chitosan, colloidal silicon dioxide, croscarmellose sodium, crospovidone, glycine, guar gum, hydroxypropyl cellulose, low-substituted hydroxypropyl cellulose, magnesium aluminum silicate, methylcellulose, povidone, sodium alginate, sodium carboxymethylcellulose, sodium starch glycolate and starch.

The pharmaceutical composition described hereinafter as Example 7B did not include any disintegrant, but surprisingly a significantly improved dissolution was nevertheless achieved vs Comparative Example 1 (the 'blend in capsule' formulation). The Example 7B composition gave 42.5% dissolution within 15 minutes, compared to just 15.8% dissolution from Comparative Example 1 at the same time point.

A further aspect of the invention provides a pharmaceutical composition containing the Agent that exhibits further improved dissolution and overall release characteristics. The pharmaceutical composition of this aspect of the invention includes a pharmaceutical disintegrant. The pharmaceutical compositions described hereinafter as Examples 7A and 7B are substantially identical except that the disintegrant of Example 7A (hydroxypropylcellulose) is substituted by additional diluent in Example 7B. As shown in the table below, at pH =6.8, the formulation of Example 7A achieved a much improved dissolution at t=15 minutes and improved release after 60 minutes vs Examples 7B and Comparative Example 1:

| Example No. | Dissolution at 15 minutes (%) | Release at 60 mins (%) |
|---|---|---|
| Comparative Ex. 1 | 15.8 | 85 |
| 7B | 42.5 | 75 |
| 7A | 89.9 | 98 |

According to this further aspect of the invention, further claims and embodiments of the invention are provided wherein the pharmaceutical composition (or pharmaceutical tablet) as defined herein has the amount of pharmaceutical disintegrant (c) limited to any of the ranges listed below:
from 1 to 15 parts by weight.
from 2 to 15 parts by weight
from 2 to 10 parts by weight
from 2 to 8 parts by weight It was surprisingly found that the use of low-substituted hydroxypropyl cellulose was particularly favourable for achieving an improved dissolution profile for the pharmaceutical tablet compositions containing the Agent. Some of the experimental pharmaceutical compositions tested involved the use of sodium starch glycolate as a disintegrant (e.g. Example 3) but it was surprisingly found that switching from sodium starch glycolate to low-substituted hydroxypropyl cellulose (Example 4) provided a significant improvement in dissolution profile, as shown in the table below:

| Example No. | Dissolution at 15 minutes (%) | Release after 30 minutes (%) |
|---|---|---|
| 3 | 69.4 | 77.3 |
| 4 | 74.7 | 83.8 |

According to this aspect of the present invention, in one embodiment the one or more pharmaceutical disintegrants (c) comprises low-substituted hydroxypropyl cellulose, sodium starch glycolate or a mixture thereof.

In one embodiment the one or more pharmaceutical disintegrants (c) comprises low-substituted hydroxypropyl cellulose.

In one embodiment the one or more pharmaceutical disintegrants (c) comprises sodium starch glycolate.

Low-substituted hydroxypropyl cellulose is commercially available from Shin Etsu Chemical Co. Ltd (Japan) and may be referred to as "LH-31". Compared to hydroxypropyl cellulose, low-substituted hydroxypropyl cellulose has only a small proportion of the three free hydroxyl groups per glucose subunit converted to a hydroxypropyl ether. When dried at 105° C. for 1 hour, low-substituted hydroxypropyl cellulose contains not less than 5.0% and not more than 16.0% of hydroxypropoxy groups.

In one embodiment low-substituted hydroxypropyl cellulose and/or sodium starch glycolate are one or two of the one or more pharmaceutical disintegrants (c) wherein the low-substituted hydroxypropyl cellulose and/or sodium starch glycolate make up from 40 to 100 wt % of the one or more pharmaceutical disintegrants (c).

In another embodiment the aforementioned range is from 50 to 100 wt %.

In another embodiment the aforementioned range is from 60 to 100 wt %.

In another embodiment the aforementioned range is from 70 to 100 wt %.

In another embodiment the aforementioned range is from 80 to 100 wt %.

In another embodiment the aforementioned range is from 90 to 100 wt %.

In one embodiment the one or more pharmaceutical disintegrants (c) consists of low-substituted hydroxylpropyl cellulose, sodium starch glycolate or a mixture thereof.

In one embodiment low-substituted hydroxypropyl cellulose is one of the one or more pharmaceutical disintegrants (c) wherein the low-substituted hydroxypropyl cellulose makes up from 40 to 100 wt % of the one or more pharmaceutical disintegrants (c).

In another embodiment the aforementioned range is from 50 to 100 wt %.

In another embodiment the aforementioned range is from 60 to 100 wt %.

In another embodiment the aforementioned range is from 70 to 100 wt %.

In another embodiment the aforementioned range is from 80 to 100 wt %.

In another embodiment the aforementioned range is from 90 to 100 wt %.

In one embodiment the one or more pharmaceutical disintegrants (c) consists of low-substituted hydroxypropyl cellulose.

In one embodiment sodium starch glycolate is one of the one or more pharmaceutical disintegrants (c) wherein the sodium starch glycolate makes up from 40 to 100 wt % of the one or more pharmaceutical disintegrants (c).

In another embodiment the aforementioned range is from 50 to 100 wt %.

In another embodiment the aforementioned range is from 60 to 100 wt %.

In another embodiment the aforementioned range is from 70 to 100 wt %.

In another embodiment the aforementioned range is from 80 to 100 wt %.

In another embodiment the aforementioned range is from 90 to 100 wt %.

In one embodiment the one or more pharmaceutical disintegrants (c) consists of sodium starch glycolate.

Pharmaceutical Solubilising Agents

In this specification the terms "solubilising agent" and "solubilising agents" are intended to be interpreted in the context of pharmaceutical formulation science. Accordingly, a solubilising agent may be, for example: benzalkonium chloride, benzyl benzoate, betadex sulfobutyl ether sodium, cetylpyridinium chloride, cyclodextrins, diethylene glycol monoethyl ether, fumaric acid, hydroxypropyl betadex, hypromellose, lanolin alcohols, lecithin, oleyl alcohol, phospholipids, poloxamer, polyoxyethylene alkyl ethers, polyoxyethylene castor oil derivatives, polyoxyethylene sorbitan fatty acid esters, polyoxyl 15 hydroxystearate, polyoxylglycerides, povidone, pyrrolidone, sodium lauryl sulfate, sorbitan esters (sorbitan fatty acid esters), tricaprylin, triolein and vitamin E polyethylene glycol succinate.

Accordingly, in one embodiment the one or more pharmaceutical solubilising agents (d) comprises one or more pharmaceutical solubilising agents selected from benzalkonium chloride, benzyl benzoate, betadex sulfobutyl ether sodium, cetylpyridinium chloride, cyclodextrins, diethylene glycol monoethyl ether, fumaric acid, hydroxypropyl betadex, hypromellose, lanolin alcohols, lecithin, oleyl alcohol, phospholipids, poloxamer, polyoxyethylene alkyl ethers, polyoxyethylene castor oil derivatives, polyoxyethylene sorbitan fatty acid esters, polyoxyl 15 hydroxystearate, polyoxylglycerides, povidone, pyrrolidone, sodium lauryl sulfate, sorbitan esters (sorbitan fatty acid esters), tricaprylin, triolein and vitamin E polyethylene glycol succinate.

In one embodiment the solubilising agent is sodium lauryl sulfate.

The pharmaceutical tablet composition described hereinafter as Example 2 included a solubilising agent (sodium lauryl sulfate) which might be expected to promote dissolution and potentially alleviate one or more of the previously mentioned problems. While on one hand the initial dissolution rate for Example 2 was improved over that of Comparative Example 1 (i.e. the simple 'blend in capsule'), the improvement was modest, providing 46.5% dissolution after 15 minutes. There was also an outstanding problem that the improved formulation of Example 2 nevertheless exhibited incomplete release of AZD9291 mesylate (only 69.1% after 60 minutes in the pH 6.8 dissolution test).

Surprisingly, it was found that a solution to the above-mentioned problems was to minimize the use of solubilising agent. As shown in the experimental section hereinafter, Examples 2 and 3 are substantially identical except that no solubilising agent was used with Example 3. As shown in the table below, the formulation of Example 3 achieved a much improved dissolution at t=15 minutes and improved release after 60 minutes, vs Example 2.

| Example No. | Dissolution at 15 minutes (%) | Release after 60 minutes (%) |
| --- | --- | --- |
| 2 | 46.5 | 69.1 |
| 3 | 69.4 | 82.1 |

According to this aspect of the invention, further claims and embodiments of the invention are provided wherein the pharmaceutical composition (or pharmaceutical tablet) as defined herein may have the amount of pharmaceutical solubilising agent (d) limited to any of the ranges listed below:

from 0 to 1 parts by weight.
from 0 to 0.75 parts by weight.
from 0 to 0.5 parts by weight.
from 0 to 0.25 parts by weight.
from 0 to 0.15 parts by weight.
from 0 to 0.1 parts by weight.
from 0 to 0.05 parts by weight.

In further aspects, claims and embodiments a pharmaceutical solubilising agent (d) is not present within the pharmaceutical composition (or pharmaceutical tablet).

Pharmaceutical Lubricants

In this specification the terms "lubricant" and "lubricants" are intended to be interpreted in the context of pharmaceutical formulation science. Accordingly, a lubricant may be, for example calcium stearate, glyceryl behenate, glyceryl dibehenate, glyceryl monostearate, glyceryl palmitostearate, a mixture of benenate esters of glycerine (e.g. a mixture of glyceryl bihenehate, tribehenin and glyceryl behenate), leucine, magnesium stearate, myristic acid, palmitic acid, poloxamer, polyethylene glycol, potassium benzoate, sodium benzoate, sodium lauryl sulfate, sodium stearate, sodium stearyl fumarate, stearic acid, talc, tribehenin and zinc stearate.

Accordingly, in one embodiment the one or more pharmaceutical lubricants (e) comprises one or more pharmaceutical lubricants selected from calcium stearate, glyceryl behenate, glyceryl dibehenate, glyceryl monostearate, glyceryl palmitostearate, a mixture of benenate esters of glycerine (e.g. a mixture of glyceryl bihenehate, tribehenin and s glyceryl behenate), leucine, magnesium stearate, myristic acid, palmitic acid, poloxamer, polyethylene glycol, potassium benzoate, sodium benzoate, sodium lauryl sulfate, sodium stearate, sodium stearyl fumarate, stearic acid, talc, tribehenin and zinc stearate.

The pharmaceutical composition described hereinafter as Example 6 did not include any lubricant, demonstrating that a lubricant may not be an essential element in io providing a pharmaceutical tablet formulation of the Agent. Nevertheless, in the context that such tablet formulations may be intended to be manufactured on a large scale for human consumption, the use of a lubricant may nevertheless be preferable in order to try to reduce the risk of physical damage to both the pharmaceutical tablets and the manufacturing equipment (for example, damage to the tablet punches). Such physical is damage has the potential to result in contamination of the pharmaceutical tablet product with small amounts of metal originating from the damaged equipment. A commonly used lubricant is magnesium stearate and we included magnesium stearate in a number of the pharmaceutical compositions described hereinafter (e.g. Examples 2, 3 and 4).

In a further aspect of the invention, the present inventors surprisingly found that the use of certain lubricants provided significantly improved dissolution characteristics for the pharmaceutical compositions of the invention. In this aspect of the invention, a particularly beneficial lubricant is sodium stearyl fumarate. Alternatively, a mixture of behenate esters of glycerine (containing glyceryl dibehenate, tribehenin and glyceryl behenate) was also found to be particularly beneficial. Comparative data demonstrating the improved dissolution characteristics vs the use of magnesium stearate is shown in the table below:

| Example No. | Lubricant | Dissolution at 7.5 minutes (%) | Release after 15 minutes (%) |
|---|---|---|---|
| 4 | Magnesium stearate | 63.0 | 74.7 |
| 5 | Sodium stearyl fumarate | 79.5 | 86.0 |
| 6B | Behenate esters of glycerine | 77.7 | 85.7 |

As shown in hereinafter in the experimental section, the formulations of Examples 4 and 5 were identical except for the difference in the identity of the lubricant substance. Similarly, the formulations of Examples 4 and 6B, except for the difference in the identity of the lubricant substance, were otherwise substantially very similar.

According to this further aspect of the invention, further claims and embodiments are provided wherein the pharmaceutical composition (or pharmaceutical tablet) as defined herein may have the amount of pharmaceutical lubricant (e) limited to any of the ranges listed below:
from 0.25 to 3 parts by weight.
from 0.5 to 3 parts by weight.
from 0.5 to 2.5 parts by weight
from 0.75 to 3 parts by weight.
from 1 to 3 parts by weight.
from 1.5 to 3 parts by weight
from 1 to 2.5 parts by weight.
from 1.5 to 2.5 parts by weight.

According to this aspect of the invention, in one embodiment the one or more pharmaceutical lubricants (e) comprises sodium stearyl fumarate, glyceryl dibehenate or a mixture thereof.

In one embodiment, the one or more pharmaceutical disintegrants (e) comprises one or more pharmaceutical disintegrants selected from sodium stearyl fumarate, glyceryl dibehenate, glyceryl behenate and tribehenin.

In one embodiment sodium stearyl fumarate and/or glyceryl dibehenate are one or two of the one or more pharmaceutical lubricants (e) wherein the sodium stearyl fumarate and/or glyceryl dibehenate make up from 30 to 100 wt % of the one or more pharmaceutical lubricants (e).

In another embodiment the aforementioned range is from 40 to 100 wt %.
In another embodiment the aforementioned range is from 50 to 100 wt %.
In another embodiment the aforementioned range is from 60 to 100 wt %.
In another embodiment the aforementioned range is from 70 to 100 wt %.
In another embodiment the aforementioned range is from 80 to 100 wt %.
In another embodiment the aforementioned range is from 90 to 100 wt %.

In another embodiment the one or more pharmaceutical lubricants (e) consists of sodium stearyl fumarate, glyceryl dibehenate or a mixture thereof.

In one embodiment the one or more pharmaceutical lubricants (e) comprises s sodium stearyl fumarate and/or one or more behenate esters of glycerine.

In one embodiment sodium stearyl fumarate and/or one or more behenate esters of glycerine are one or more of the one or more pharmaceutical lubricants (e) wherein the sodium stearyl fumarate and/or the one or more behenate esters of glycerine make up from 30 to 100 wt % of the one or more pharmaceutical lubricants (e).

In another embodiment the aforementioned range is from 40 to 100 wt %.
In another embodiment the aforementioned range is from 50 to 100 wt %.
In another embodiment the aforementioned range is from 60 to 100 wt %.
In another embodiment the aforementioned range is from 70 to 100 wt %.
In another embodiment the aforementioned range is from 80 to 100 wt %.
In another embodiment the aforementioned range is from 90 to 100 wt %.

In another embodiment the one or more pharmaceutical lubricants (e) consists of sodium stearyl fumarate and/or one or more behenate esters of glycerine or a mixture thereof.

In another embodiment the one or more pharmaceutical lubricants (e) consists of sodium stearyl fumarate, glyceryl dibehenate, glyceryl behenate, tribehenin or any mixture thereof.

In one embodiment the one or more pharmaceutical lubricants (e) comprises sodium stearyl fumarate.

In one embodiment sodium stearyl fumarate is one of the one or more pharmaceutical lubricants (e) wherein the sodium stearyl fumarate makes up from 30 to 100 wt % of the one or more pharmaceutical lubricants (e).

In another embodiment the aforementioned range is from 40 to 100 wt %.

In another embodiment the aforementioned range is from 50 to 100 wt %.

In another embodiment the aforementioned range is from 60 to 100 wt %.

In another embodiment the aforementioned range is from 70 to 100 wt %.

In another embodiment the aforementioned range is from 80 to 100 wt %.

In another embodiment the aforementioned range is from 90 to 100 wt %.

In another embodiment the one or more pharmaceutical lubricants (e) consists of sodium stearyl fumarate.

In one embodiment the one or more pharmaceutical lubricants (e) comprises one or more behenate esters of glycerine. (i.e. one or more of glyceryl dibehenate, tribehenin and glyceryl behenate).

In one embodiment one or more behenate esters of glycerine is one or more of the one or more pharmaceutical lubricants (e) wherein the one or more behenate esters of glycerine makes up from 30 to 100 wt % of the one or more pharmaceutical lubricants (e).

In another embodiment the aforementioned range is from 40 to 100 wt %.

In another embodiment the aforementioned range is from 50 to 100 wt %.

In another embodiment the aforementioned range is from 60 to 100 wt %.

In another embodiment the aforementioned range is from 70 to 100 wt %.

In another embodiment the aforementioned range is from 80 to 100 wt %.

In another embodiment the aforementioned range is from 90 to 100 wt %.

In another embodiment the one or more pharmaceutical lubricants (e) consists of one or more behenate esters of glycerine.

In one embodiment the one or more pharmaceutical lubricants (e) comprises glyceryl dibehenate.

In one embodiment the one or more pharmaceutical lubricants (e) comprises one or more behenate esters of glycerine.

In one embodiment one or more behenate esters of glycerine is one or more of the one or more pharmaceutical lubricants (e) wherein the one or more behenate esters of glycerine makes up from 30 to 100 wt % of the one or more pharmaceutical lubricants (e).

In another embodiment the aforementioned range is from 40 to 100 wt %.

In other embodiment the aforementioned range is from 50 to 100 wt %.

In another embodiment the aforementioned range is from 60 to 100 wt %.

In another embodiment the aforementioned range is from 70 to 100 wt %.

In another embodiment the aforementioned range is from 80 to 100 wt %.

In another embodiment the aforementioned range is from 90 to 100 wt %.

In another embodiment the one or more pharmaceutical lubricants (e) consists of one or more behenate esters of glycerine.

Interpretation

In this specification, the word "comprising" describes components that must be present, but leaves open the possibility that other unspecified components may also be present within the scope of the relevant term.

In this specification, the word "consisting" describes components of the invention that must be present but does not leave open the possibility that other unspecified additional components may also be present within the scope of the relevant term.

Accordingly, for example, in the first aspect of the invention, as defined hereinabove where "comprising" is used, the fact that (a)+(b)+(c)+(d)+(e)=100 does not prevent other unspecified pharmaceutically relevant components from being present within the pharmaceutical composition. Such additional components might include, for example, a pharmaceutically acceptable colourant or other pharmaceutically acceptable substances that might be included as part of a tablet coating.

The skilled person will appreciate that certain pharmaceutical excipients may be used in anhydrate form or in one or more hydrated forms. For example lactose may be used as an anhydrous form or as a monohydrate. Similarly, dibasic calcium phosphate may be used as the anhydrate form or as the dihydrate form. In this specification, where the hydration level of any pharmaceutical excipients is not explicitly mentioned, it is to be interpreted that any and all conventional hydration levels are encompassed by the term. Therefore, "lactose" (without further qualification) includes lactose monohydrate, lactose in the anhydrate form and mixtures thereof. In a similar way, the skilled person will appreciate that calcium phosphate may be used in a dibasic form or a tribasic form. In this specification, "calcium phosphate" (without further qualification) includes the dibasic form, the tribasic form and mixtures thereof.

The Pharmaceutical Composition and a Pharmaceutical Tablet

The pharmaceutical composition of the present invention is intended to be formed into pharmaceutical tablets suitable for oral administration to a human being. This may be achieved via a dry mixing / direct compression process as described in more detail in the experimental section hereinafter.

Accordingly, in one aspect there is provided a pharmaceutical tablet comprising the pharmaceutical composition as defined herein.

In one embodiment there is provided a pharmaceutical tablet comprising a tablet core wherein the tablet core comprises the pharmaceutical composition as defined herein and wherein the tablet core has a coating. In one embodiment the coating is a film coating.

When the tablet has a film coating, the film coating may be applied using conventional methods. A coating can be used to provide protection against, for example, moisture ingress or degradation by light, to colour the formulation, or to modify or control the release of the Agent from the formulation.

Suitable coatings, such as film coatings, that may be applied to the composition according to the invention comprise a film-forming agent, for example a sugar or more particularly a film-forming polymer. Suitable sugar coatings are well known and comprise for example sucrose or lactose. Suitable film-forming agents include, for example film-forming polymers, such as cellulose ethers, esters and mixed ethers and esters, including esters of water-soluble cellulose ethers, for example hydroxypropyl methylcellulose, hydroxypropyl ethylcellulose, hydroxypropylcellulose, methylcellulose, hydroxypropyl methylcellulose acetate succinate or hydroxypropyl methylcellulose phthalate; film-forming acrylic polymers, for example methacrylate-methylmethacrylate copolymers; and film-forming vinyl polymers, for example polyvinyl alcohols or polyvinyl acetate phthalate. Suitably the film-forming polymer is a water-soluble film-forming polymer, particularly a water-soluble cellulose ether for example hydroxypropyl methylcellulose (particularly hydroxypropyl methylcellulose with a dynamic viscosity of from 2 to 18 cP (measured in a 2% w/v solution at 20° C.) and selected from, for example grades 1828, 2208, 2906 and especially 2910 as defined hereinbefore). The amount of film-forming agent used will depend upon the desired properties of the film coating. Generally the film forming agent will be present in an amount of from 40 to 90% by weight of the film coating, for example from 50 to 80% of the film coating. The film-forming agent is typically present at from 0.5 to 5%, suitably from 2.5 to 5% by weight of the formulation according to the invention.

Optionally the film coating contains additional components such as plasticiser, colorants, dispersion aids and opacifiers. Plasticisers may be used to improve film flexibility and durability and adhesion properties of the film coating. Suitable plasticisers include, for example glycerin, acetylated monoglycerides, citrate esters (for example triethyl citrate), propylene glycols, polyethylene glycols (for example polyethylene glycols with a molecular weight of from 200 to 500, particularly 300), triacetin (glycerol triacetate), triglycerides (for example castor oil), or phthalate esters (for example diethylphthalate). Generally the plasticiser, when used, is present in an amount of from 1 to 20%, for example 5 to 15% by weight based upon the weight of the film coating.

Suitable opacifiers and colorants are well known and include for example titanium dioxide, ferric oxides (for example iron oxide).

Suitable dispersion aids include, for example talc.

In an embodiment of the invention the film coating comprises
  (i) from 50 to 100 (suitably from 50 to 80 parts of a water-soluble cellulose ether (suitably hydroxypropyl methylcellulose, particularly hydroxypropyl methylcellulose with a dynamic viscosity of from 2 to 18 cP (measured in a 2% w/v solution at 20° C.), for example grades 2910, 1828, 2208 or 2906 as defined hereinbefore with a dynamic viscosity of from 5 to 7 cP);
  (ii) from 0 to 25 (particularly from 5 to 20) parts plasticiser (suitably polyethylene glycol, particularly polyethylene glycol with a molecular weight of from 200 to 500); and
  (iii) from 0 to 50 (particularly from 0 to 30) parts in total of opacifiers (suitably titanium dioxide), colorants (suitably an iron oxide) and dispersion aids;
  wherein all parts are by weight and the sum of the parts (i)+(ii)+(iii)=100.

The coating may comprise, for example, 0.5 to 10% by weight of the composition, particularly 1 to 6%, and preferably 2.5 to 5%. Suitable film coatings are commercially available as concentrates that may be diluted with water and optionally a cellulose ether such as HPMC and a plasticiser such as polyethylene glycol prior to application to the composition. Such concentrates include Opaspray™ coatings from Colorcon, for example Opaspray™ Brown M-1-25092 and Opaspray Yellow M-1-22842.

In one embodiment the film coating comprises a water-soluble cellulose ether and/or an ester of a water-soluble cellulose ether.

In one embodiment the film coating comprises a water-soluble cellulose ether.

In one embodiment the film coating comprises hydroxypropyl methylcellulose.

In one embodiment the film coating is hydroxypropyl methylcellulose-based.

An example of a suitable hydroxylpropyl methylcellulose-based film coating is commercially available from Colorcon under the trade name "Opadry II", for example "Opadry II beige".

In one embodiment there is provided a pharmaceutical tablet consisting of a tablet core that has a film coating; wherein the tablet core consists of the pharmaceutical composition as defined herein.

In any claim, aspect or embodiment of the invention where the 'pharmaceutical composition' is mentioned, the following embodiments may also be applied, unless the context otherwise requires, in order to provide further claims, aspects or embodiments:

In one embodiment the pharmaceutical composition is a pharmaceutical tablet composition (for oral administration).

In one embodiment the pharmaceutical composition of the present invention is a pharmaceutical tablet composition suitable for oral administration to a human.

In one embodiment the pharmaceutical composition of the present invention is a pharmaceutical tablet composition suitable for oral administration to a human who has cancer [particularly lung cancer, more particularly non-small cell lung cancer (NSCLC), for example EGFRM+NSCLC].

In one embodiment the pharmaceutical composition of the present invention is a pharmaceutical tablet composition suitable for oral administration to a human who has EGFRM+ and T790M+ non-small cell lung cancer.

In any claim, aspect or embodiment of the invention where the 'pharmaceutical tablet' is mentioned, the following embodiments may also be applied in order to provide further claims, aspects or embodiments:

In one embodiment the pharmaceutical tablet has a weight in the range from 25 to 1500 mg.

In one embodiment the pharmaceutical tablet has a weight in the range from 30 to 1200 mg.

In one embodiment the pharmaceutical tablet has a weight in the range from 40 to 1000 mg.

In one embodiment the pharmaceutical tablet has a weight in the range from 75 to 750 mg.

In any claim, aspect or embodiment of the invention where the 'pharmaceutical composition' or 'pharmaceutical tablet' is mentioned, the following embodiments may also be applied in order to provide further claims, aspects or embodiments:

In one embodiment the combined weight of the components (a), (b), (c), (d) and (e), as defined herein, is greater than or equal to 75% of the total weight of the pharmaceutical composition.

In one embodiment the combined weight of the components (a), (b), (c), (d) and (e), as defined herein, is greater than or equal to 75% of the total weight of the pharmaceutical tablet.

In one embodiment the combined weight of the components (a), (b), (c), (d) and (e), as defined herein, is greater than or equal to 85% of the total weight of the pharmaceutical composition.

In one embodiment the combined weight of the components (a), (b), (c), (d) and (e), as defined herein, is greater than or equal to 85% of the total weight of the pharmaceutical tablet.

In one embodiment the combined weight of the components (a), (b), (c), (d) and (e), as defined herein, is greater than or equal to 90% of the total weight of the pharmaceutical composition.

In one embodiment the combined weight of the components (a), (b), (c), (d) and (e), as defined herein, is greater than or equal to 90% of the total weight of the pharmaceutical tablet.

In one embodiment the combined weight of the components (a), (b), (c), (d) and (e), as defined herein, is greater than or equal to 95% of the total weight of the pharmaceutical composition.

In one embodiment the combined weight of the components (a), (b), (c), (d) and (e), as defined herein, is greater than or equal to 95% of the total weight of the pharmaceutical tablet.

In one embodiment the combined weight of the components (a), (b), (c), (d) and (e), as defined herein, is greater than or equal to 97.5% of the total weight of the pharmaceutical composition.

In one embodiment the combined weight of the components (a), (b), (c), (d) and (e), as defined herein, is greater than or equal to 97.5% of the total weight of the pharmaceutical tablet.

In a further aspect of the invention there is provided the use of a pharmaceutical composition, as defined herein, for the manufacture of a medicament.

In one embodiment there is provided the use of a pharmaceutical composition, as defined herein, for the manufacture of a medicament for the treatment of cancer.

In one aspect of the invention there is provided a pharmaceutical composition, as defined herein, for use as a medicament.

In one embodiment there is provided a pharmaceutical tablet, as defined herein, for use as a medicament.

In one embodiment there is provided a pharmaceutical composition, as defined herein, for use in the treatment of cancer.

In one embodiment there is provided a pharmaceutical tablet, as defined herein, for use in the treatment of cancer.

In one aspect of the invention there is provided a method of treating cancer in a patient in need thereof, which method comprises the oral administration of an effective amount of the pharmaceutical composition, as defined herein, to the patient.

In one embodiment the patient is a warm-blooded mammal.

In another embodiment the patient is a human patient.

In another embodiment the patient is an adult human patient.

In one embodiment there is provided a method of treating cancer in a patient in need thereof, which method comprises the oral administration of an effective number of the pharmaceutical tablet(s), as defined herein, to the patient.

In any aspect, embodiment or claim where "cancer" is mentioned in this specification, the cancer may be further defined according to the embodiments listed below, unless such a definition would be inappropriate in a particular context:

In one embodiment the cancer is lung cancer.

In one embodiment the cancer is non-small cell lung cancer.

In one embodiment the cancer is EGFR-mutation positive non-small cell lung cancer.

In one embodiment the cancer is T790M+ non-small cell lung cancer.

In one embodiment the cancer is EGFRM+ and T790M+ non-small cell lung cancer.

Further Embodiments of the Invention

In this specification it is intended that any number of range-limitations, embodiments, aspects or claims, as defined hereinbefore or hereinafter, may be combined together (unless the context provides that a given combination would be inappropriate) in order to provide further embodiments and claims of the invention. For example, such combinations may combine to provide further embodiments as defined below.

In one embodiment there is provided a pharmaceutical composition comprising:
(a) from 2 to 70 parts of the Agent;
(b) from 5 to 96 parts of two or more pharmaceutical diluents;
(c) from 0 to 15 parts of one or more pharmaceutical disintegrants;
(d) from 0 to 1.5 parts of one or more pharmaceutical solubilising agents; and
(e) from 0.5 to 3 parts of one or more pharmaceutical lubricants;
wherein all parts are by weight and the sum of the parts (a)+(b)+(c)+(d)+(e)=100; wherein one of the two or more pharmaceutical diluents is microcrystalline cellulose wherein the microcrystalline cellulose makes up from 7 to 30 wt % of the two or more pharmaceutical diluents (b).

In one embodiment there is provided a pharmaceutical composition comprising:
(a) from 2 to 70 parts of the Agent;
(b) from 5 to 96 parts of two or more pharmaceutical diluents;
(c) from 0 to 15 parts of one or more pharmaceutical disintegrants;
(d) from 0 to 1.5 parts of one or more pharmaceutical solubilising agents; and
(e) from 0.5 to 3 parts of one or more pharmaceutical lubricants;
wherein all parts are by weight and the sum of the parts (a)+(b)+(c)+(d)+(e)=100; wherein one of the two or more pharmaceutical diluents is microcrystalline cellulose wherein the microcrystalline cellulose makes up from 7 to 30 wt % of the two or more pharmaceutical diluents (b); and wherein the one or more pharmaceutical lubricants (e) comprises sodium stearyl fumarate and/or one or more behenate esters of glycerine.

In one embodiment there is provided a pharmaceutical composition comprising:
(a) from 2 to 70 parts of the Agent;
(b) from 5 to 96 parts of two or more pharmaceutical diluents;
(c) from 2 to 15 parts of one or more pharmaceutical disintegrants;
(d) from 0 to 1.5 parts of one or more pharmaceutical solubilising agents; and
(e) from 0.5 to 3 parts of one or more pharmaceutical lubricants;
wherein all parts are by weight and the sum of the parts (a)+(b)+(c)+(d)+(e)=100; wherein one of the two or more pharmaceutical diluents is microcrystalline cellulose wherein the microcrystalline cellulose makes up from 7 to 30 wt % of the two or more pharmaceutical diluents (b).

In one embodiment there is provided a pharmaceutical composition comprising:
(a) from 2 to 70 parts of the Agent;
(b) from 5 to 96 parts of two or more pharmaceutical diluents;
(c) from 2 to 15 parts of one or more pharmaceutical disintegrants;
(d) from 0 to 0.75 parts of one or more pharmaceutical solubilising agents; and (e) from 0.5 to 3 parts of one or more pharmaceutical lubricants;

wherein all parts are by weight and the sum of the parts (a)+(b)+(c)+(d)+(e)=100; wherein one of the two or more pharmaceutical diluents is microcrystalline cellulose wherein the microcrystalline cellulose makes up from 7 to 30 wt % of the two or more pharmaceutical diluents (b).

In one embodiment there is provided a pharmaceutical composition comprising:
(a) from 5 to 50 parts of the Agent;
(b) from 5 to 96 parts of two or more pharmaceutical diluents;
(c) from 2 to 15 parts of one or more pharmaceutical disintegrants;
(d) from 0 to 0.75 parts of one or more pharmaceutical solubilising agents; and
(e) from 0.5 to 3 parts of one or more pharmaceutical lubricants;

wherein all parts are by weight and the sum of the parts (a)+(b)+(c)+(d)+(e)=100; wherein one of the two or more pharmaceutical diluents is microcrystalline cellulose wherein the microcrystalline cellulose makes up from 7 to 30 wt % of the two or more pharmaceutical diluents (b).

In one embodiment there is provided a pharmaceutical composition comprising:
(a) from 5 to 50 parts of the Agent;
(b) from 55 to 85 parts of two or more pharmaceutical diluents;
(c) from 2 to 15 parts of one or more pharmaceutical disintegrants;
(d) from 0 to 0.75 parts of one or more pharmaceutical solubilising agents; and
(e) from 0.5 to 3 parts of one or more pharmaceutical lubricants;

wherein all parts are by weight and the sum of the parts (a)+(b)+(c)+(d)+(e)=100; wherein one of the two or more pharmaceutical diluents is microcrystalline cellulose wherein the microcrystalline cellulose makes up from 7 to 30 wt % of the two or more pharmaceutical diluents (b).

In one embodiment there is provided a pharmaceutical composition comprising:
(a) from 5 to 50 parts of the Agent;
(b) from 5 to 96 parts of two or more pharmaceutical diluents;
(c) from 2 to 15 parts of one or more pharmaceutical disintegrants;
(d) from 0 to 0.75 parts of one or more pharmaceutical solubilising agents; and
(e) from 0.5 to 3 parts of one or more pharmaceutical lubricants;

wherein all parts are by weight and the sum of the parts (a)+(b)+(c)+(d)+(e)=100; wherein one of the two or more pharmaceutical diluents is microcrystalline cellulose wherein the microcrystalline cellulose makes up from 7 to 30 wt % of the two or more pharmaceutical diluents (b); and wherein the one or more pharmaceutical disintegrants (c) comprises low-substituted hydroxypropyl cellulose.

In one embodiment there is provided a pharmaceutical composition comprising:
(a) from 5 to 50 parts of the Agent;
(b) from 5 to 96 parts of two or more pharmaceutical diluents;
(c) from 2 to 15 parts of one or more pharmaceutical disintegrants;
(d) from 0 to 0.75 parts of one or more pharmaceutical solubilising agents; and
(e) from 0.5 to 3 parts of one or more pharmaceutical lubricants;

wherein all parts are by weight and the sum of the parts (a)+(b)+(c)+(d)+(e)=100; wherein one of the two or more pharmaceutical diluents is microcrystalline cellulose wherein the microcrystalline cellulose makes up from 7 to 30 wt % of the two or more pharmaceutical diluents (b); and wherein the one or more pharmaceutical disintegrants (c) comprises low-substituted hydroxypropyl cellulose; and wherein the one or more pharmaceutical lubricants (e) comprises sodium stearyl fumarate and/or one or more behenate esters of glycerine.

In one embodiment there is provided a pharmaceutical composition comprising:
(a) from 5 to 50 parts of the Agent;
(b) from 55 to 85 parts of two or more pharmaceutical diluents;
(c) from 2 to 15 parts of one or more pharmaceutical disintegrants;
(d) from 0 to 0.75 parts of one or more pharmaceutical solubilising agents; and
(e) from 0.5 to 3 parts of one or more pharmaceutical lubricants;

wherein all parts are by weight and the sum of the parts (a)+(b)+(c)+(d)+(e)=100; wherein one of the two or more pharmaceutical diluents is microcrystalline cellulose wherein the microcrystalline cellulose makes up from 7 to 30 wt % of the two or more pharmaceutical diluents (b); and wherein the one or more pharmaceutical disintegrants (c) comprises low-substituted hydroxypropyl cellulose.

In one embodiment there is provided a pharmaceutical composition comprising:
(a) from 5 to 50 parts of the Agent;
(b) from 55 to 85 parts of two or more pharmaceutical diluents;
(c) from 2 to 15 parts of one or more pharmaceutical disintegrants;
(d) from 0 to 0.75 parts of one or more pharmaceutical solubilising agents; and
(e) from 0.5 to 3 parts of one or more pharmaceutical lubricants;

wherein all parts are by weight and the sum of the parts (a)+(b)+(c)+(d)+(e)=100; wherein one of the two or more pharmaceutical diluents is microcrystalline cellulose wherein the microcrystalline cellulose makes up from 7 to 30 wt % of the two or more pharmaceutical diluents (b); and wherein the one or more pharmaceutical disintegrants (c) comprises low-substituted hydroxypropyl cellulose and wherein the one or more pharmaceutical lubricants (e) comprises sodium stearyl fumarate and/or one or more behenate esters of glycerine.

In one embodiment there is provided a pharmaceutical composition comprising:
(a) from 5 to 50 parts of the Agent;
(b) from 5 to 96 parts of two or more pharmaceutical diluents;
(c) from 2 to 15 parts of one or more pharmaceutical disintegrants;
(d) from 0 to 0.75 parts of one or more pharmaceutical solubilising agents; and
(e) from 0.5 to 3 parts of one or more pharmaceutical lubricants;

wherein all parts are by weight and the sum of the parts (a)+(b)+(c)+(d)+(e)=100; wherein one of the two or more pharmaceutical diluents is microcrystalline cellulose wherein the microcrystalline cellulose makes up from 7 to 30 wt % of the two or more pharmaceutical diluents (b); wherein the Agent is the mesylate salt of AZD9291.

In one embodiment there is provided a pharmaceutical composition comprising:
(a) from 5 to 50 parts of the Agent;
(b) from 5 to 96 parts of two or more pharmaceutical diluents;
(c) from 2 to 15 parts of one or more pharmaceutical disintegrants;
(d) from 0 to 0.75 parts of one or more pharmaceutical solubilising agents; and
(e) from 0.5 to 3 parts of one or more pharmaceutical lubricants;
wherein all parts are by weight and the sum of the parts (a)+(b)+(c)+(d)+(e)=100;
wherein one of the two or more pharmaceutical diluents is microcrystalline cellulose wherein the microcrystalline cellulose makes up from 7 to 30 wt % of the two or more pharmaceutical diluents (b) and wherein in addition to microcrystalline cellulose, the other pharmaceutical diluent(s) within the two or more pharmaceutical diluents is/are selected from cellulose acetate, erythritol, ethylcellulose, fructose, inulin, isomalt, lactitol, lactose, maltitol, maltodextrin, maltose, mannitol, polydextrose, polyethylene glycol, pullulan, simethicone, sodium chloride, sorbitol, starch, sucrose, trehalose and xylitol; and wherein the one or more pharmaceutical disintegrants (c) comprises low-substituted hydroxypropyl cellulose and wherein the one or more pharmaceutical lubricants (e) comprises sodium stearyl fumarate and/or one or more behenate esters of glycerine; and wherein the Agent is the mesylate salt of AZD9291.

In one embodiment there is provided a pharmaceutical composition comprising:
(a) from 5 to 50 parts of the Agent;
(b) from 5 to 96 parts of two or more pharmaceutical diluents;
(c) from 2 to 15 parts of one or more pharmaceutical disintegrants;
(d) from 0 to 0.75 parts of one or more pharmaceutical solubilising agents; and
(e) from 0.5 to 3 parts of one or more pharmaceutical lubricants;
wherein all parts are by weight and the sum of the parts (a)+(b)+(c)+(d)+(e)=100;
wherein one of the two or more pharmaceutical diluents is microcrystalline cellulose wherein the microcrystalline cellulose makes up from 7 to 30 wt % of the two or more pharmaceutical diluents (b); wherein the Agent is the mesylate salt of AZD9291, and wherein in addition to microcrystalline cellulose, the other pharmaceutical diluent(s) within the two or more pharmaceutical diluents is/are selected from cellulose acetate, erythritol, ethylcellulose, fructose, inulin, isomalt, lactitol, lactose, maltitol, maltodextrin, maltose, mannitol, polydextrose, polyethylene glycol, pullulan, simethicone, sodium chloride, sorbitol, starch, sucrose, trehalose and xylitol.

LIST OF FIGURES

FIGS. 1 to 6 show dissolution data that was obtained using the United States Pharmacopoeia methodology that is described hereinafter in the experimental section.

FIG. 1: Dissolution profile for Examples 1 to 5 (pH 6.8)
FIG. 2: Dissolution profile for Examples 6A, 6B, 6C and 6D (pH 6.8)
FIG. 3: Expanded dissolution profile for Examples 6A, 6B, 6C and 6D (pH 6.8)
FIG. 4: Dissolution profile for Examples 7A, 7B, 8A and 8B (pH 6.8)
FIG. 5: Dissolution profile for Example 9 (80 mg, pH 6.8)
FIG. 6: Dissolution profile for Example 9 (pH 1.3)

EXPERIMENTAL DETAILS

Dissolution Tests

The dissolution described herein were performed according to the general procedure of the United States Pharmacopoeia using Apparatus II (paddle), with either 900 mL of pH 6.8 phosphate buffer (50 mM $NaH_2PO_4$) or pH 1.3 media (2 g/L of NaCl adjusted to pH 1.3 with either HCl or NaOH) at a temperature of 37° C. 10 mL samples of the dissolution media were withdrawn at 7.5, 15, 20, 30, 45 and 60 minutes, filtered through a glass fibre syringe filter (Acrodisc glass fibre GxF part number 4529 or equivalent), discarding the first 4 mL. The concentration of drug substance in the remaining solution was quantified by UV analysis at a wavelength of 335 nm (pH 6.8) or 270 nm (pH 1.3) versus a standard solution. Generally, the dissolution results disclosed in this specification are based on an average of three repeated tests.

Materials used in Examples

The materials used in the Examples described hereinafter are shown in the table below:

| Material | Grade | Supplier |
| --- | --- | --- |
| Cellulose, microcrystalline | Avicel™ PH-102 | FMC Biopolymer (Ireland) |
| Behenate esters of glycerine | Compitrol 888 ATO[#] | Gattefosse S.A. (France) |
| Lactose monohydrate | Pharmatose 450M | DFE Pharma (Germany) |
| Low-substituted hydroxypropyl cellulose | LH-31 | Shin Etsu Chemical Co. Ltd. (Japan) |
| Magnesium stearate | NF Non Bovine | Mallinckrodt (USA) |
| Mannitol | Pearlitol 200SD | Roquette Freres S.A. (France) |
| Sodium lauryl sulphate (Sodium dodecyl sulfate) | Kolliphor | BASF/Cognis (Germany) |
| Sodium starch glycolate | Glycolys LV | Roquette Freres S.A. (France) |
| Sodium stearyl fumarate | Pruv | JRS Pharma (Germany) |

[#]Compitrol 888 ATO is described as a mixture of glycerol esters including glyceryl dibehenate, tribehenin and glyceryl behenate.

COMPARATIVE EXAMPLE 1

'Blend in Capsule' Formulation

AZD9291 mesylate was blended with microcrystalline cellulose in the ratio 1:2 by weight is and filled into opaque, white, size 0 HPMC capsules such that each capsule contained the equivalent of 20 mg AZD9291 free base. The quantitative composition of this 'blend in capsule' formulation is shown in the table below:

| Components | Quantities | | |
|---|---|---|---|
| | (g per batch) | (mg/capsule) | (wt %) |
| AZD9291 mesylate | 26.20 | 23.80[a] | 29.75 |
| Microcrystalline cellulose | 61.80 | 56.20 | 70.25 |
| Total | 88.00 | 80.00 | 100.00 |

[a]Equivalent to 20 mg of AZD9291 free base

EXAMPLE 2

This tablet formulation was manufactured using a dry mixing / direct compression process. AZD9291 mesylate was dry mixed with the excipients listed in the table below (excluding the magnesium stearate) using a Turbula T2 blender at a speed of 28 rpm for 30 minutes. The magnesium stearate was added to the mix and blending continued for a further 5 minutes at 28 rpm. The dry mix was compressed to form 200 mg tablets using a Riva single station mini-press equipped with 8 mm round concave punches. The quantitative composition of this tablet formulation is shown in the table below:

| Components | Quantities | | | Function |
|---|---|---|---|---|
| | (g per batch) | (mg/tablet) | (wt %) | |
| AZD9291 mesylate | 8.93 | 23.80[a] | 11.90 | Drug substance |
| Lactose monohydrate | 45.50 | 121.28 | 60.64 | Diluent |
| Microcrystalline cellulose | 15.00 | 39.98 | 19.99 | Diluent |
| Sodium starch glycolate | 3.75 | 10.00 | 5.00 | Disintegrant |
| Magnesium stearate | 0.75 | 2.00 | 1.00 | Lubricant |
| Sodium lauryl sulphate | 1.13 | 2.94 | 1.47 | Solubilising Agent |
| Total | 75.06 | 200.00 | 100.00 | |

[a]Equivalent to 20 mg of AZD9291 free base

EXAMPLE 3

This tablet formulation was manufactured using the process described above for Example 2. The quantitative composition of this tablet formulation is shown in the table below:

| Components | Quantities | | | Function |
|---|---|---|---|---|
| | (g per batch) | (mg/tablet) | (wt %) | |
| AZD9291 mesylate | 11.90 | 23.80[a] | 11.90 | Drug substance |
| Mannitol | 62.10 | 124.20 | 62.10 | Diluent |
| Microcrystalline cellulose | 20.00 | 40.00 | 20.00 | Diluent |
| Sodium starch glycolate | 5.00 | 10.00 | 5.00 | Disintegrant |
| Magnesium stearate | 1.00 | 2.00 | 1.00 | Lubricant |
| Total | 100.00 | 200.00 | 100.00 | |

[a]Equivalent to 20 mg of AZD9291 free base

EXAMPLE 4

This tablet formulation was manufactured using the process described above for Example 2. The quantitative composition of this tablet formulation is shown in the table below:

| Components | Quantities | | | Function |
|---|---|---|---|---|
| | (g per batch) | (mg/tablet) | (wt %) | |
| AZD9291 mesylate | 11.90 | 23.80[a] | 11.90 | Drug substance |
| Mannitol | 62.10 | 124.20 | 62.10 | Diluent |
| Microcrystalline cellulose | 20.00 | 40.00 | 20.00 | Diluent |
| Low-substituted hydroxypropyl cellulose | 5.00 | 10.00 | 5.00 | Disintegrant |
| Magnesium stearate | 1.00 | 2.00 | 1.00 | Lubricant |
| Total | 100.00 | 200.00 | 100.00 | |

[a]Equivalent to 20 mg of AZD9291 free base

EXAMPLE 5

This tablet formulation was manufactured using the process described above for Example 2. The quantitative composition of this tablet formulation is shown in the table below:

| Components | Quantities | | | Function |
| --- | --- | --- | --- | --- |
| | (g per batch) | (mg/tablet) | (wt %) | |
| AZD9291 mesylate | 11.90 | 23.80[a] | 11.90 | Drug substance |
| Mannitol | 62.10 | 124.20 | 62.10 | Diluent |
| Microcrystalline cellulose | 20.00 | 40.00 | 20.00 | Diluent |
| Low-substituted hydroxypropyl cellulose | 5.00 | 10.00 | 5.00 | Disintegrant |
| Sodium stearyl fumarate | 1.00 | 2.00 | 1.00 | Lubricant |
| Total | 100.00 | 200.00 | 100.00 | |

[a]Equivalent to 20 mg of AZD9291 free base

EXAMPLE 6A

This tablet formulation was manufactured using a dry mixing/roller compaction process using the materials listed in the table below. The AZD9291 mesylate, mannitol, microcrystalline cellulose and hydroxypropyl cellulose were first mixed using a Turbula T2 blender at a speed of 28 rpm for 30 minutes. A portion of the sodium stearyl fumarate (0.5% of the batch weight) was added and mixing continued using the same parameters for a further 5 minutes. The mixture was roller compacted using an Alexanderwerk bench top roller compactor with a roller pressure of 40 bar, a gap size of 2 mm, a roller speed of 10.1-10.2 rpm (25mm rollers) and a screw speed of 22.4-22.9 rpm. The resulting ribbon was milled using a Comil U3 with a granulator speed of 100 rpm and a screen size of 1.27 mm. The resulting granules were returned to the Turbula T2 blender, the remaining sodium stearyl fumarate added, and mixing continued at 28 rpm for 5 minutes. This dry mix was compressed to form 500 mg tablets using a Riva classic rotary press equipped with 14.5×7.25 mm punches.

| Components | Quantities | | | Function |
| --- | --- | --- | --- | --- |
| | (g per batch) | (mg/tablet) | (wt %) | |
| AZD9291 mesylate | 9.52 | 95.36 | 19.07 | Drug substance |
| Mannitol | 32.48 | 324.64 | 64.93 | Diluent |
| Microcrystalline cellulose | 5.00 | 50.00 | 10.00 | Diluent |
| Low-substituted hydroxypropyl cellulose | 2.50 | 25.00 | 5.00 | Disintegrant |
| Sodium stearyl fumarate | 0.50 | 5.00 | 1.00 | Lubricant |
| Total | 50.00 | 500.00 | 100.00 | |

EXAMPLE 6B

This tablet formulation was manufactured using a dry mixing/roller compaction process using the materials listed in the table below. The AZD9291 mesylate, mannitol, microcrystalline cellulose and hydroxypropyl cellulose were first mixed using a Turbula T2 blender at a speed of 28 rpm for 30 minutes. A portion of the behenate esters of glycerine (0.5% of the batch weight) was added and mixing continued using the same parameters for a further 5 minutes. The mixture was roller compacted using an Alexanderwerk bench top roller compactor with a roller pressure of 40 bar, a gap size of 2 mm, a roller speed of 10.1-10.2 rpm (25 mm rollers) and a screw speed of 22.4-22 rpm. The resulting ribbon was milled using a Comil U3 with a granulator speed of 100 rpm and a screen size of 1.27 mm. The resulting granules were returned to the Turbula T2 blender, the remaining behenate esters of glycerine added, and mixing continued at 28 rpm for 5 minutes. This dry mix was compressed to form 200 mg tablets using a Riva single station press equipped with 7 mm concave punches.

| | Quantities | | | |
|---|---|---|---|---|
| Components | (g per batch) | (mg/tablet) | (wt %) | Function |
| AZD9291 mesylate | 9.52 | 38.08 | 19.04 | Drug substance |
| Mannitol | 32.48 | 129.92 | 64.96 | Diluent |
| Microcrystalline cellulose | 5.00 | 20.00 | 10.00 | Diluent |
| Low substituted hydroxypropyl cellulose | 2.50 | 10.00 | 5.00 | Disintegrant |
| Behenate esters of glycerine | 0.50 | 2.00 | 1.00 | Lubricant |
| Total | 50.00 | 200.00 | 100.00 | |

EXAMPLE 6C

This tablet formulation was manufactured using a dry mixing/roller compaction process using the materials listed in the table below. The AZD9291 mesylate, mannitol, microcrystalline cellulose and hydroxypropyl cellulose were first mixed using a Turbula T2 blender at a speed of 28 rpm for 30 minutes. The mixture was roller compacted using an Alexanderwerk bench top roller compactor with a roller pressure of 40 bar, a gap size of 2 mm, a roller speed of 10.1-10.2 rpm (25 mm rollers) and a screw speed of 22.4-22.9 rpm. The resulting ribbon was milled using a Comil U3 with a granulator speed of 100 rpm and a screen size of 1.27 mm. This dry mix was compressed to form 200 mg tablets using a Riva single station press equipped with 7 mm concave punches.

| | Quantities | | | |
|---|---|---|---|---|
| Components | (g per batch) | (mg/tablet) | (wt %) | Function |
| AZD9291 mesylate | 9.52 | 38.08 | 19.04 | Drug substance |
| Mannitol | 32.98 | 131.92 | 65.96 | Diluent |
| Microcrystalline cellulose | 5.00 | 20.00 | 10.00 | Diluent |
| Low substituted hydroxypropyl cellulose | 2.50 | 10.00 | 5.00 | Disintegrant |
| Total | 50.00 | 200.00 | 100.00 | |

EXAMPLE 6D

This tablet formulation was manufactured using a dry mixing/roller compaction process using the materials listed in the table below. The AZD9291 mesylate, mannitol, microcrystalline cellulose and hydroxypropyl cellulose were first mixed using a Turbula T2 blender at a speed of 28 rpm for 30 minutes. A portion of the sodium stearyl fumarate (0.5% of the batch weight) was added and mixing continued using the same parameters for a further 5 minutes. The mixture was roller compacted using an Alexanderwerk bench top roller compactor with a roller pressure of 40 bar, a gap size of 2 mm, a roller speed of 10.1-10.2 rpm (25 mm rollers) and a screw speed of 22.4-22.9 rpm. The resulting ribbon was milled using a Comil U3 with a granulator speed of 100 rpm and a screen size of 1.27 mm. The resulting granules were returned to the Turbula T2 blender, the remaining sodium stearyl fumarate added, and mixing continued at 28 rpm for 5 minutes. This dry mix was compressed to form 500 mg tablets using a Riva classic rotary press equipped with 14.5×7.25 mm punches.

| | Quantities | | | |
|---|---|---|---|---|
| Components | (g per batch) | (mg/tablet) | (wt %) | Function |
| AZD9291 mesylate | 26.20 | 94.25 | 18.85 | Drug substance |
| Mannitol | 90.77 | 326.50 | 65.30 | Diluent |
| Microcrystalline cellulose | 13.76 | 49.50 | 9.90 | Diluent |
| Low-substituted hydroxypropyl cellulose | 5.50 | 19.80 | 3.96 | Disintegrant |
| Sodium stearyl fumarate | 2.77 | 9.95 | 1.99 | Lubricant |
| Total | 139.00 | 500.00 | 100.00 | |

EXAMPLE 7A

This tablet formulation was manufactured using a dry mixing/roller compaction process using the materials listed in the table below. The AZD9291 mesylate, mannitol, microcrystalline cellulose and hydroxypropyl cellulose were first mixed using a Turbula T2 blender at a speed of 28 rpm for 30 minutes. A portion of the sodium stearyl fumarate (0.5% of the batch weight) was added and mixing continued using the same parameters for a further 5 minutes. The mixture was roller compacted using an Alexanderwerk bench top roller compactor with a roller pressure of 40 bar, a gap size of 2 mm, a roller speed of 10.1-10.2rpm (25 mm rollers) and a screw speed of 22.4-22.9 rpm. The resulting ribbon was milled using a Comil U3 with a granulator speed of 100 rpm and a screen size of 1.27 mm. The resulting granules were returned to the Turbula T2 blender, the remaining sodium stearyl fumarate added, and mixing continued at 28 rpm for 5 minutes. This dry mix was compressed to form 500 mg tablets using a Riva classic rotary press equipped with 14.5×7.25 mm punches.

| Components | Quantities (g per batch) | (mg/tablet) | (wt %) | Function |
|---|---|---|---|---|
| AZD9291 mesylate | 9.53 | 95.36[a] | 19.07 | Drug substance |
| Mannitol | 29.84 | 298.39 | 59.68 | Diluent |
| Microcrystalline cellulose | 7.50 | 75.00 | 15.00 | Diluent |
| Low-substituted hydroxypropyl cellulose | 2.50 | 25.00 | 5.00 | Disintegrant |
| Sodium stearyl fumarate | 0.63 | 6.25 | 1.25 | Lubricant |
| Total | 50.00 | 500.00 | 100.00 | |

[a] Equivalent to 80 mg of AZD9291 free base

EXAMPLE 7B

This tablet formulation was manufactured using a dry mixing/roller compaction process using the materials listed in the table below. The AZD9291 mesylate, mannitol, microcrystalline cellulose and hydroxypropyl cellulose were first mixed using a Turbula is T2 blender at a speed of 28 rpm for 30 minutes. A portion of the sodium stearyl fumarate (0.5% of the batch weight) was added and mixing continued using the same parameters for a further 5 minutes. The mixture was roller compacted using an Alexanderwerk bench top roller compactor with a roller pressure of 40 bar, a gap size of 2 mm, a roller speed of 10.1-10.2 rpm (25 mm rollers) and a screw speed of 22.4-22.9 rpm. The resulting ribbon was milled using a Comil U3 with a granulator speed of 100 rpm and a screen size of 1.27 mm. The resulting granules were returned to the Turbula T2 blender, the remaining sodium stearyl fumarate added, and mixing continued at 28 rpm for 5 minutes. This dry mix was compressed to form 500 mg tablets using a Riva classic rotary press equipped with 14.5×7.25 mm punches.

| Components | Quantities (g per batch) | (mg/tablet) | (wt %) | Function |
|---|---|---|---|---|
| AZD9291 mesylate | 9.54 | 95.36[a] | 19.07 | Drug substance |
| Mannitol | 32.34 | 323.39 | 64.68 | Diluent |
| Microcrystalline cellulose | 7.50 | 75.00 | 15.00 | Diluent |
| Sodium stearyl fumarate | 0.63 | 6.25 | 1.25 | Lubricant |
| Total | 50.00 | 500.00 | 100.00 | |

[a] Equivalent to 80 mg of AZD9291 free base

EXAMPLE 8A and 8B

These tablet formulations were manufactured using a dry mixing/roller compaction process using the materials listed in the tables below. The AZD9291 mesylate, mannitol, microcrystalline cellulose and hydroxypropyl cellulose were first mixed using a Muller Blender (25 litre drum) at 15 rpm for 58 minutes. A portion of the sodium stearyl fumarate (0.5% of the batch weight) was added and mixing continued using the same parameters for a further 9.5 minutes. The mixture was roller compacted using an Alexanderwerk bench top roller compactor with a roller pressure of 40 bar, a gap size of 2 mm, a roller speed of 10.1-10.2 rpm (25mm rollers) and a screw speed of 22.4-22.9 rpm. The resulting ribbon is was milled using a Comil U3 with a granulator speed of 100 rpm and a screen size of 1.27 mm. The resulting granules were returned to the Muller Blender, the remaining sodium stearyl fumarate added, and mixing continued at 15 rpm for 5 minutes. Tablet cores were compressed using a Riva Picolla rotary press equipped with 7 mm (20 mg strength) or 14.5×7.25 mm (80 mg strength) punches with a turret speed of 20 rpm.

The resulting tablet cores were coated with a proprietary film coat (Opadry II beige, supplied by Colorcon UK Ltd) at a level of 4% of the core weight, to give coated tablets with a nominal weight of 130 mg (20mg strength) and 520 mg (80 mg strength) for Examples 8A and 8B respectively. The quantitative composition of the tablet core (prior to coating) of Example 8A is shown in the table below:

| Components | Quantities | | | Function |
|---|---|---|---|---|
| | (g per batch) | (mg/tablet) | (wt %) | |
| AZD9291 mesylate | 448.19 | 23.84$^a$ | 19.07 | Drug substance |
| Mannitol | 1402.43 | 74.60 | 59.68 | Diluent |
| Microcrystalline cellulose | 352.50 | 18.75 | 15.00 | Diluent |
| Low-substituted hydroxypropyl cellulose | 117.50 | 6.25 | 5.00 | Disintegrant |
| Sodium stearyl fumarate | 29.38 | 1.56 | 1.25 | Lubricant |
| Total | 2350.00 | 125.00 | 100.00 | |

$^a$Equivalent to 20 mg of AZD9291 free base

The quantitative composition of the tablet core (prior to coating) of Example 8B is shown in the table below:

| Components | Quantities | | | Function |
|---|---|---|---|---|
| | (g per batch) | (mg/tablet) | (wt %) | |
| AZD9291 mesylate | 448.19 | 95.36$^a$ | 19.07 | Drug substance |
| Mannitol | 1402.43 | 298.39 | 59.68 | Diluent |
| Microcrystalline cellulose | 352.50 | 75.00 | 15.00 | Diluent |
| Low-substituted hydroxypropyl cellulose | 117.50 | 25.00 | 5.000 | Disintegrant |
| Sodium stearyl fumarate | 29.38 | 6.25 | 1.25 | Lubricant |
| Total | 2350.00 | 500.00 | 100.00 | |

$^a$Equivalent to 80 mg of AZD9291 free base

EXAMPLE 9

This tablet formulation was manufactured using a dry mixing / roller compaction process as described in Example 8A and 8B using the materials listed in the tables below. Tablet cores were compressed using a Riva Classic rotary press equipped with 9 mm (40 mg strength) or 14.5×7.25 mm (80 mg strength) punches with a turret speed of 20 rpm.

The resulting tablet cores were coated with a proprietary film coat (Opadry II beige, supplied by Colorcon UK Ltd) at a level of 4% of the core weight, to give coated tablets with a nominal weight of 520 mg (80 mg strength) and at a level of 5% of the core weight, to give coated tablets with a nominal weight of 262.5 mg (40 mg strength). The quantitative composition of the tablet core (prior to coating) of Example 9 is shown in the table below:

| Components | Quantities | | | Function |
|---|---|---|---|---|
| | (mg/tablet) | (mg/tablet) | (wt %) | |
| AZD9291 mesylate | 47.68$^a$ | 95.36$^b$ | 19.07 | Drug substance |
| Mannitol | 147.32 | 294.65 | 58.93 | Diluent |
| Microcrystalline cellulose | 37.50 | 75.00 | 15.00 | Diluent |

-continued

| Components | Quantities | | | Function |
|---|---|---|---|---|
| | (mg/tablet) | (mg/tablet) | (wt %) | |
| Low-substituted hydroxypropyl cellulose | 12.50 | 25.00 | 5.000 | Disintegrant |
| Sodium stearyl fumarate | 5.00 | 10.00 | 2.00 | Lubricant |
| Total | 250.00 | 500.00 | 100.00 | |

[a]Equivalent to 40 mg of AZD9291 free base
[b]Equivalent to 80 mg of AZD9291 free base

The invention claimed is:
1. A pharmaceutical composition comprising:
 (a) from 2 to 70 parts of the mesylate salt of N-(2-{2-dimethylaminoethyl-methylamino}-4-methoxy-5-{[4-(1-methylindo-3-yl)pyrimidin-2-yl]amino}phenyl)prop-2-enamide;
 (b) from 5 to 96 parts of two or more pharmaceutical diluents;
 (c) from 2 to 15 parts of one or more pharmaceutical disintegrants;
 (d) from 0 to 0.75 parts of one or more pharmaceutical solubilising agents; and
 (e) from 0 to 3 parts of one or more pharmaceutical lubricants;
wherein all parts are by weight and the sum of the parts (a)+(b)+(c)+(d)+(e)=100; and
wherein one of the two or more pharmaceutical diluents is microcrystalline cellulose wherein the microcrystalline cellulose makes up from 7 to 30 wt % of the two or more pharmaceutical diluents (b).

2. The pharmaceutical composition according to claim 1 wherein the pharmaceutical composition comprises from 1 to 2.5 parts of the one or more pharmaceutical lubricants (e).

3. The pharmaceutical composition according to claim 2 wherein the one or more pharmaceutical lubricants (e) comprises sodium stearyl fumarate and/or one or more behenate esters of glycerine.

4. The pharmaceutical composition according to claim 3, wherein the pharmaceutical composition comprises from 2 to 10 parts of the one or more pharmaceutical disintegrants (c).

5. The pharmaceutical composition according to claim 4 wherein the one or more pharmaceutical disintegrants (c) comprises low-substituted hydroxypropyl cellulose.

6. The pharmaceutical composition according to claim 5, wherein the pharmaceutical composition comprises from 0 to 0.25 parts of one or more pharmaceutical solubilising agents (d).

7. The pharmaceutical composition according to claim 6, wherein the pharmaceutical composition comprises from 5 to 50 parts of the mesylate salt of N-(2-{2-dimethylaminoethyl-methylamino}-4-methoxy-5-{[4-(1-methylindol-3-yl)pyrimidin-2-yl]amino}phenyl)prop-2-enamide.

8. A method of treating cancer in a patient in need thereof, which method comprises the oral administration to the patient of an effective amount of the pharmaceutical composition as claimed in claim 1.

9. A pharmaceutical tablet comprising the pharmaceutical composition as claimed in claim 1.

10. A pharmaceutical tablet comprising a tablet core wherein the tablet core comprises the pharmaceutical composition as claimed in claim 1, wherein the tablet core has a coating.

11. A method of treating cancer in a patient in need thereof, which method comprises the oral administration of an effective number of the pharmaceutical tablet(s), as claimed in claim 9, to the patient.

12. The method of claim 8, wherein the cancer is non-small cell lung cancer.

13. The method of claim 11, wherein the cancer is non-small cell lung cancer.

14. The pharmaceutical composition as claimed in claim 6, wherein a pharmaceutical solubilising agent (d) is not present.

15. The pharmaceutical composition as claimed in claim 7, wherein the pharmaceutical composition comprises from 7 to 30 parts of the mesylate salt of N-(2-{2-dimethylaminoethyl-methylamino}-4-methoxy-5-{[4-(1-methylindo-3-yl)pyrimidin-2-yl]amino}phenyl)prop-2-enamide.

16. A pharmaceutical composition as claimed in claim 1 comprising:
 (a) from 5 to 50 parts of the mesylate salt of N-(2-{2-dimethylaminoethyl-methylamino}-4-methoxy-5-{[4-(1-methylindol-3-yl)pyrimidin-2-yl]amino}phenyl)prop-2-enamide;
 (b) from 5to 96 parts of two or more pharmaceutical diluents;
 (c) from 2 to 15 parts of one or more pharmaceutical disintegrants;
 (d) from 0 to 0.75 parts of one or more pharmaceutical solubilising agents; and
 (e) from 0.5 to 3 parts of one or more pharmaceutical lubricants;
wherein all parts are by weight and the sum of the parts (a)+(b)+(c)+(d)+(e)=100;
wherein one of the two or more pharmaceutical diluents is microcrystalline cellulose wherein the microcrystalline cellulose makes up from 7 to 30 wt % of the two or more pharmaceutical diluents (b) and wherein in addition to microcrystalline cellulose, the other pharmaceutical diluent(s) within the two or more pharmaceutical diluents is/are selected from cellulose acetate, erythritol, ethylcellulose, fructose, inulin, isomalt, lactitol, lactose, maltitol, maltodextrin, maltose, mannitol, polydextrose, polyethylene glycol, pullulan, simethicone, sodium chloride, sorbitol, starch, sucrose, trehalose and xylitol; and wherein the one or more pharmaceutical disintegrants (c) comprises low-substituted hydroxypropyl cellulose and wherein the one or more pharmaceutical lubricants (e) comprises sodium stearyl fumarate and/or one or more behenate esters of glycerine.

17. A method of treating cancer in a patient in need thereof, which method comprises the oral administration to the patient of an effective amount of the pharmaceutical composition as claimed in claim 16.

18. A pharmaceutical tablet comprising the pharmaceutical composition as claimed in claim 16.

19. A pharmaceutical tablet comprising a tablet core wherein the tablet core comprises the pharmaceutical composition as claimed in claim 16, wherein the tablet core has a coating.

20. A method of treating cancer in a patient in need thereof, which method comprises the oral administration of an effective number of the pharmaceutical tablet(s), as claimed in claim 19, to the patient.

21. A pharmaceutical composition according to claim 1 comprising:
- (a) from 7 to 25 parts of the mesylate salt of N-(2-{2-dimethylaminoethyl-methylamino}-4-methoxy-5-{[4-(1-methylindol-3-yl)pyrimidin-2-yl]amino}phenyl) prop-2-enamide;
- (b) from 55 to 85 parts of two pharmaceutical diluents;
- (c) from 2 to 8 parts of a pharmaceutical disintegrant; and
- (e) from 1.5 to 2.5 parts of a pharmaceutical lubricant;

wherein a pharmaceutical solubilising agent (d) is not present; wherein all parts are by weight and the sum of the parts (a)+(b)+(c)+(e)=100; and wherein one of the two pharmaceutical diluents is microcrystalline cellulose wherein the microcrystalline cellulose makes up from 7 to 30 wt % of the two pharmaceutical diluents (b).

22. A pharmaceutical composition according to claim 21 comprising:
- (a) from 7 to 25 parts of the mesylate salt of N-(2-{2-dimethylaminoethyl-methylamino}-4-methoxy-5-{[4-(1-methylindol-3-yl)pyrimidin-2-yl]amino}phenyl) prop-2-enamide;
- (b) from 55 to 85 parts of two pharmaceutical diluents, wherein the pharmaceutical diluents are microcrystalline cellulose and mannitol;
- (c) from 2 to 8 parts of a pharmaceutical disintegrant, wherein the pharmaceutical disintegrant is low-substituted hydroxypropyl cellulose; and
- (e) from 1.5 to 2.5 parts of a pharmaceutical lubricant, wherein the pharmaceutical lubricant is sodium stearyl fumarate;

wherein a pharmaceutical solubilising agent (d) is not present; wherein all parts are by weight and the sum of the parts (a)+(b)+(c)+(e)=100; and wherein the microcrystalline cellulose makes up from 7 to 30 wt % of the two pharmaceutical diluents (b).

23. A pharmaceutical composition according to claim 22 comprising:
- (a) about 19 parts of the mesylate salt of N-(2-{2-dimethylaminoethyl-methylamino}-4-methoxy-5-{[4-(1-methylindol-3-yl)pyrimidin-2-yl]amino}phenyl) prop-2-enamide;
- (b) about 59 parts of mannitol;
- (c) about 15 parts of microcrystalline cellulose;
- (d) about 5 parts of low-substituted hydroxypropyl cellulose; and
- (e) about 2 parts of sodium stearyl fumarate.

\* \* \* \* \*